(12) United States Patent
Weinschenk et al.

(10) Patent No.: US 9,791,443 B2
(45) Date of Patent: Oct. 17, 2017

(54) METHOD FOR DIFFERENTIALLY QUANTIFYING NATURALLY PROCESSED HLA-RESTRICTED PEPTIDES FOR CANCER, AUTOIMMUNE AND INFECTIOUS DISEASES IMMUNOTHERAPY DEVELOPMENT

(75) Inventors: Toni Weinschenk, Aichwald (DE); Jens Fritsche, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 1427 days.

(21) Appl. No.: 13/087,948

(22) Filed: Apr. 15, 2011

(65) Prior Publication Data

US 2011/0257890 A1    Oct. 20, 2011

Related U.S. Application Data

(60) Provisional application No. 61/324,941, filed on Apr. 16, 2010.

(30) Foreign Application Priority Data

Apr. 16, 2010 (GB) ................ 1006360.0

(51) Int. Cl.
| | |
|---|---|
| *G01N 33/48* | (2006.01) |
| *G01N 33/569* | (2006.01) |
| *G01N 33/68* | (2006.01) |
| *G06G 7/58* | (2006.01) |

(52) U.S. Cl.
CPC ... *G01N 33/56977* (2013.01); *G01N 33/6842* (2013.01); *G01N 33/6848* (2013.01); *G01N 33/6878* (2013.01); *G01N 2333/70539* (2013.01)

(58) Field of Classification Search
CPC ........ G06N 19/18; G06N 19/20; G06N 19/22; G06N 19/24; G06N 19/32; G06N 19/4273

See application file for complete search history.

(56) References Cited

FOREIGN PATENT DOCUMENTS

| EP | 1508047 | 8/2008 |
|---|---|---|
| WO | 03/025576 | 3/2003 |
| WO | 2005/076009 | 8/2005 |

OTHER PUBLICATIONS

M. Fortier, et al., "The MHC class I peptide repertoire is molded by the transcriptome", JEM, Mar. 17, 2008, vol. 205, No. 3, pp. 595-610.

H. Singh-Jasuja, et al., "The Tubingen approach: identification, selection, and validation of tumor-associated HLA peptides for cancer therapy", Cancer Immunol Immunother, (2004), vol. 53, pp. 187-195.

B. Moritz, et al., "Approaches for quantification of protein concentration ratios", Proteomics, 2003, vol. 3, pp. 2208-2220.

*Primary Examiner* — Eric S Dejong
(74) *Attorney, Agent, or Firm* — McBee Moore Woodward & Vanik IP, LLC; Susan McBee

(57) ABSTRACT

The invention relates to a method for quantitatively identifying relevant HLA-bound peptide antigens from primary tissue specimens on a large scale without labeling approaches. This method can not only be used for the development of peptide vaccines, but is also highly valuable for a molecularly defined immunomonitoring and the identification of new antigens for any immunotherapeutic strategy in which HLA-restricted antigenic determinants function as targets, such as a variety of subunit vaccines or adoptive T-cell transfer approaches in cancer, or infectious and autoimmune diseases.

12 Claims, 12 Drawing Sheets

C

D a)

LC-MS runs of sample 969

SEQUENCE LISTING

<160> NUMBER OF SEQ ID NOS: 27

<210> SEQ ID NO 1
<211> LENGTH: 10
<212> TYPE: PRT
<213> ORGANISM: Homo sapiens

<400> SEQUENCE: 1

Leu Tyr Gln Ile Leu Gln Gly Ile Val Phe
1               5                   10

<210> SEQ ID NO 2
<211> LENGTH: 9
<212> TYPE: PRT
<213> ORGANISM: Homo sapiens

<400> SEQUENCE: 2

Ser Tyr Asn Pro Leu Trp Leu Arg Ile
1               5

<210> SEQ ID NO 3
<211> LENGTH: 9
<212> TYPE: PRT
<213> ORGANISM: Homo sapiens

<400> SEQUENCE: 3

Val Phe Ile Phe Lys Gly Asn Gln Phe
1               5

<210> SEQ ID NO 4

```
<211> LENGTH: 9
<212> TYPE: PRT
<213> ORGANISM: Homo sapiens

<400> SEQUENCE: 4

Ser Tyr Ile Asp Val Leu Pro Glu Phe
1               5

<210> SEQ ID NO 5
<211> LENGTH: 9
<212> TYPE: PRT
<213> ORGANISM: Homo sapiens

<400> SEQUENCE: 5

Asn Tyr Leu Pro Phe Ile Met Glu Leu
1               5

<210> SEQ ID NO 6
<211> LENGTH: 9
<212> TYPE: PRT
<213> ORGANISM: Homo sapiens

<400> SEQUENCE: 6

Asn Tyr Leu Leu Tyr Val Ser Asn Phe
1               5

<210> SEQ ID NO 7
<211> LENGTH: 10
<212> TYPE: PRT
<213> ORGANISM: Homo sapiens

<400> SEQUENCE: 7

Ile Tyr Asn Gly Lys Leu Phe Asp Leu Leu
1               5                   10

<210> SEQ ID NO 8
<211> LENGTH: 9
<212> TYPE: PRT
<213> ORGANISM: Homo sapiens

<400> SEQUENCE: 8

His Tyr Lys Pro Thr Pro Leu Tyr Phe
1               5

<210> SEQ ID NO 9
<211> LENGTH: 10
<212> TYPE: PRT
<213> ORGANISM: Homo sapiens

<400> SEQUENCE: 9

Val Trp Ser Asp Val Thr Pro Leu Thr Phe
1               5                   10

<210> SEQ ID NO 10
<211> LENGTH: 9
<212> TYPE: PRT
<213> ORGANISM: Homo sapiens

<400> SEQUENCE: 10

Asn Tyr Leu Leu Tyr Val Ser Asn Phe
1               5

<210> SEQ ID NO 11
<211> LENGTH: 9
<212> TYPE: PRT
```

```
<213> ORGANISM: Homo sapiens

<400> SEQUENCE: 11

Val Tyr Thr Thr Ser Tyr Gln Gln Ile
1               5

<210> SEQ ID NO 12
<211> LENGTH: 9
<212> TYPE: PRT
<213> ORGANISM: Homo sapiens

<400> SEQUENCE: 12

Arg Tyr Leu Trp Ala Thr Val Thr Ile
1               5

<210> SEQ ID NO 13
<211> LENGTH: 9
<212> TYPE: PRT
<213> ORGANISM: Homo sapiens

<400> SEQUENCE: 13

Gln Tyr Ala Ser Arg Phe Val Gln Leu
1               5

<210> SEQ ID NO 14
<211> LENGTH: 9
<212> TYPE: PRT
<213> ORGANISM: Homo sapiens

<400> SEQUENCE: 14

Thr Tyr Gly Asn Leu Leu Asp Tyr Leu
1               5

<210> SEQ ID NO 15
<211> LENGTH: 9
<212> TYPE: PRT
<213> ORGANISM: Homo sapiens

<400> SEQUENCE: 15

Ala Tyr Ala Ile Ile Lys Glu Glu Leu
1               5

<210> SEQ ID NO 16
<211> LENGTH: 9
<212> TYPE: PRT
<213> ORGANISM: Homo sapiens

<400> SEQUENCE: 16

Phe Tyr Ile Ser Pro Val Asn Lys Leu
1               5

<210> SEQ ID NO 17
<211> LENGTH: 10
<212> TYPE: PRT
<213> ORGANISM: Homo sapiens

<400> SEQUENCE: 17

Lys Tyr Asn Asp Thr Phe Trp Lys Glu Phe
1               5                   10

<210> SEQ ID NO 18
<211> LENGTH: 9
<212> TYPE: PRT
<213> ORGANISM: Homo sapiens
```

```
<400> SEQUENCE: 18

Asn Tyr Glu Glu Thr Phe Pro His Ile
1               5

<210> SEQ ID NO 19
<211> LENGTH: 9
<212> TYPE: PRT
<213> ORGANISM: Homo sapiens

<400> SEQUENCE: 19

Val Tyr Gly Ile Arg Leu Glu His Phe
1               5

<210> SEQ ID NO 20
<211> LENGTH: 9
<212> TYPE: PRT
<213> ORGANISM: Homo sapiens

<400> SEQUENCE: 20

Arg Phe Leu Ser Gly Ile Ile Asn Phe
1               5

<210> SEQ ID NO 21
<211> LENGTH: 9
<212> TYPE: PRT
<213> ORGANISM: Homo sapiens

<400> SEQUENCE: 21

Ala Tyr Leu Val Tyr Thr Asp Arg Leu
1               5

<210> SEQ ID NO 22
<211> LENGTH: 10
<212> TYPE: PRT
<213> ORGANISM: Homo sapiens

<400> SEQUENCE: 22

Val Phe Asp Thr Ala Ile Ala His Leu Phe
1               5                   10

<210> SEQ ID NO 23
<211> LENGTH: 10
<212> TYPE: PRT
<213> ORGANISM: Homo sapiens

<400> SEQUENCE: 23

Tyr Tyr Asn Ala Ala Gly Phe Asn Lys Leu
1               5                   10

<210> SEQ ID NO 24
<211> LENGTH: 9
<212> TYPE: PRT
<213> ORGANISM: Homo sapiens

<400> SEQUENCE: 24

Val Tyr Lys Val Val Gly Asn Leu Leu
1               5

<210> SEQ ID NO 25
<211> LENGTH: 9
<212> TYPE: PRT
<213> ORGANISM: Homo sapiens

<400> SEQUENCE: 25
```

```
Val Tyr Ile Glu Lys Asn Asp Lys Leu
1               5

<210> SEQ ID NO 26
<211> LENGTH: 10
<212> TYPE: PRT
<213> ORGANISM: Homo sapiens

<400> SEQUENCE: 26

Glu Leu Ala Gly Ile Gly Ile Leu Thr Val
1               5                   10

<210> SEQ ID NO 27
<211> LENGTH: 9
<212> TYPE: PRT
<213> ORGANISM: Homo sapiens

<400> SEQUENCE: 27

Tyr Leu Leu Pro Ala Ile Val His Ile
1               5
```

METHOD FOR DIFFERENTIALLY QUANTIFYING NATURALLY PROCESSED HLA-RESTRICTED PEPTIDES FOR CANCER, AUTOIMMUNE AND INFECTIOUS DISEASES IMMUNOTHERAPY DEVELOPMENT

RELATED APPLICATIONS

This application claims priority to UK patent application GB1006360.0, filed on Apr. 16, 2010, and U.S. Provisional Patent Application No. 61/324,941, filed on Apr. 16, 2010, the entire contents of which are hereby incorporated by reference.

BACKGROUND OF THE INVENTION

Field of the Invention

The present invention relates to a method for quantitatively identifying relevant HLA-bound peptide antigens from primary tissue specimens on a large scale. This method can not only be used for the development of peptide vaccines, but is also highly valuable for a molecularly defined immuno-monitoring and the identification of new antigens for any immunotherapeutic strategy in which HLA-restricted antigenic determinants function as targets, such as a variety of subunit vaccines or adoptive T-cell transfer approaches in cancer, or infectious and autoimmune diseases.

Description of the Related Art

Development of cancer immuno-therapeutics and immuno-therapies of autoimmune and infectious diseases aiming to induce the immune system's T-cell arm to fight cancer might be substantially improved by a profound knowledge of human leukocyte antigen (HLA)-bound peptide presentation levels on primary malignant tissues. This information is relevant for peptide vaccines in particular as well as for any other type of T-cell vaccine based on molecular entities such as protein, DNA or RNA. This kind of quantitative data has not been available on an "omics"-scale before, because common quantitation methods have so far mostly relied on differential chemical labeling strategies requiring that all samples to be compared are processed within a single experiment, which severely limited the possible scale of such investigations.

A method for identifying peptides a above avoiding the "reverse immunology"-associated problem was disclosed in EP1508047B1. As described above, this method can not be used for the quantitation of said peptides. Another method employing a labeling strategy was disclosed in WO 2005/076009 which allowed for some quantitation, but not on a larger scale. Other labels were disclosed, for example, in WO 03/025576 or by Martin et al in Proteomics 2003, 3, 2208-2220.

Another method was disclosed by Fortier et al (The MHC class I peptide repertoire is molded by the transcriptome, JEM, Vol. 205, No. 3, Mar. 17, 2008 595-610). This method has the disadvantages that it requires the dissection of MHC-bound peptides from non-MHC-binding peptides due to acid elution. This is performed using b2m-knockout cell lines: Thus, this method can not be used for primary—patient—tumour materials. In the method, primary murine thymocytes were compared to the murine EL4 cell line. The starting amounts had been adjusted by measuring MHC I molecules. This alone is a strong restriction of the method disclosed by Fortier et al. Furthermore, a normalization as it would be required for primary tissues of different sizes and tissue origin was not applied. Rather, balanced starting materials were used making normalization obsolete. However, normalization is absolutely necessary for primary (patient) materials.

Stimulation of an immune response is dependent upon the presence of antigens recognized as foreign by the host immune system. The discovery of the existence of tumor associated and disease antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defenses against cancer. CD8-positive T-cells (T-CD8$^+$) in particular, which recognize peptides bound to class I molecules of the major histocompatibility complex (MHC). These peptides of usually 8 to 10 amino acid residues are derived from proteins or defective ribosomal products (DRIPS) located in the cytosol, play an important role in this response. Human MHC-molecules are also designated as human leukocyte-antigens (HLA).

There are two classes of MHC-molecules: MHC class I molecules that can be found on most cells having a nucleus. MHC molecules are composed of a alpha heavy chain and beta-2-microglobulin (MHC class I receptors) or an alpha and a beta chain (MHC class II receptors), respectively. Their three-dimensional conformation results in a binding groove, which is used for non-covalent interaction with peptides. MHC class I present peptides that result from proteolytic cleavage of predominantly endogenous proteins, DRIPs and larger peptides. MHC class II molecules can be found predominantly on professional antigen presenting cells (APCs), and primarily present peptides of exogenous or transmembrane proteins that are taken up by APCs during the course of endocytosis, and are subsequently processed. Complexes of peptide and MHC class I molecules are recognized by CD8-positive cytotoxic T-lymphocytes bearing the appropriate TCR (T-cell receptor), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

For a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules being expressed by tumor cells, they also have to be recognized by T cells bearing specific T cell receptors (TCR).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated or disease associated antigens comprises the following major groups:

Cancer-testis antigens: The first TAAs [tumor-associated antigens; disease-associated antigens are abbreviated DAA] ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, Survivin, Telomerase or WT1.

Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

TAAs arising from abnormal post-translational modifications: Such TAAs may arise from proteins which are neither specific nor over-expressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens or disease-specific or -associated antigens, and to be used in a therapy, particular prerequisites must be fulfilled. The antigen should be expressed mainly by tumor cells or infected cells and not at all or only in comparably small amounts by normal healthy tissues, for example less by the factor 5, 10 or more.

In infectious diseases there are two possibilities, first the infected cells express an antigen not expressed by healthy cells—directly associated to the infection—or the infected cells over-express an antigen expressed only in very small amounts by healthy cells—the over-expression of an antigen normally found in the peptidome of a healthy cell.

It is furthermore desirable, that the respective antigen is not only present in a type of tumor, infection or strain, but also in high concentrations (i.e. copy numbers of the respective peptide per cell). Tumor-specific and tumor-associated antigens and disease-specific or disease-associated antigens are often derived from proteins directly involved in transformation of a normal cell to a tumor/infected cell due to a function e.g. in cell cycle control or suppression of apoptosis.

In the case of cancer, additional downstream targets of the proteins directly causative for a transformation may be upregulated and thus may be indirectly tumor-associated. Such indirect tumor-associated antigens may also be targets of a vaccination approach (Singh-Jasuja H., Emmerich N. P., Rammensee H. G., Cancer Immunol. Immunother. 2004 March; 453 (3): 187-95). In both cases, it is essential that epitopes are present in the amino acid sequence of the antigen, since such a peptide ("immunogenic peptide") that is derived from a tumor associated or disease associated antigen should lead to an in vitro or in vivo T-cell-response.

Basically, any peptide which is able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs and DAAs are a starting point for the development of a tumor vaccine. The methods for identifying and characterizing the TAAs and DAAs are based on the use of CTL that can be isolated from patients or healthy subjects, or they are based on the generation of differential transcription profiles or differential peptide expression patterns between tumors and normal tissues.

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell which upon stimulation with a specific antigen can be clonally expanded and is able to execute effector functions ("effector T cell").

T-helper cells play an important role in orchestrating the effector function of CTLs in anti-tumor immunity. T-helper cell epitopes that trigger a T-helper cell response of the $T_{H1}$ type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions which stimulate anti-tumor immune responses.

BRIEF SUMMARY OF THE INVENTION

In view of the above, it is therefore the object of the present invention to provide a method which, at least in part:
- allows a handling of (human) tissue samples of different amounts and MHC expression levels, i.e. can be readily applied to primary tissue samples;
- is not restricted to cells for which, for example, beta2m-knockout counterparts have to be generated, i.e. is also applicable to primary (human) tissue samples;
- can be performed on a "high-throughput" level; and
- can be performed incrementally, i.e. increasing an existing dataset of quantitative data with data of new samples over years.

In a first aspect of the present invention, the object of the invention is solved by a method for the identification and label-free quantification of MHC ligand peptides on primary tissue samples from at least one mammal, comprising
a) providing at least one diseased primary tissue sample and at least one sample of primary healthy tissue preferably corresponding to the diseased tissue,
b) isolating MHC ligand peptides from said sample(s),
c) performing an HPLC-MS analysis on said MHC ligand peptides,
d) extracting the precursor ion signal intensity (area) for each signal, as derived from step c),
e) identifying the sequences of said MHC ligand peptides by fragment spectra clustering and database search, in order to group areas between different runs and samples, and normalizing areas within replicate runs to compensate technical performance/sensitivity differences between replicate runs resulting in average quantities for each peptide per sample including error estimates,
f) assigning of said sequences to MHC alleles in order to generate allele-specific sequence subgroups for a comparison between different samples, and normalizing between different samples using the allele-specific subgroups to account for different sample sizes or MHC expression levels: result is relative quantities comparable between samples,
g) performing a data quality control based on peptide reproducibility for every sample, verifying that the total number of identified sequences and the number of sequences with small variance in areas is as high as possible,
h) calculating presentation profiles and scores in order to determine a potential over-presentation of MHC ligand peptides,
i) controlling the quality of identifications and area estimates, for example by visual inspection of the peptide identification results and of the area reproducibilites, or statistical analysis,
j) comparing the values detected in said at least one diseased primary tissue sample with the value(s) obtained from said at least one primary healthy tissues, and
k) quantifying said MHC ligand peptides In a second aspect of the present invention, the object of the invention is solved by a method for identifying and quantifying MHC ligand peptides on primary tissue samples, comprising
a) providing at least one diseased tissue sample and at least one sample of healthy tissue preferably corresponding to the diseased tissue from at least one mammal,
b) isolating MHC ligand peptides from said sample(s),
c) performing a HPLC-MS analysis on said MHC ligand peptides,
d) extracting the precursor ion signal intensity (area) for each signal, as derived from step c),
e) identifying the sequences of said MHC ligand peptides by fragment spectra clustering and database search, in order to group areas between different runs and samples, and normalizing areas within replicate runs to compensate technical performance/sensitivity differences between replicate runs resulting in average quantities for each peptide per sample including error estimates,
f) assigning of said sequences to MHC alleles in order to generate allele-specific sequence subgroups for a comparison between different samples, and normalizing between different samples using the allele-specific subgroups to account for different sample sizes or MHC expression levels: result is relative quantities comparable between samples,
g) performing a data quality control based on peptide reproducibility, verifying that the total number of identified sequences and the number of sequences with small variance in area is at least 25, preferably 50, and more preferably 100,
h) calculating presentation profiles and scores in order to determine a potential over-presentation of MHC ligand peptides,
i) controlling the quality of identifications and area estimates by statistical analysis,
j) comparing the values detected in said at least one diseased primary tissue sample with the value(s) obtained from said at least one healthy tissues, and
k) quantifying said MHC ligand peptides.

Other objects and advantages of the present invention will become readily apparent for the person of skill when studying the following description as provided.

In the following description, the invention is described using cancer as an example. Nevertheless, the inventive method can also be applied in infectious diseases, autoimmune diseases, and parasitic infections as long as the respective immune answer is a MHC class I involving answer. The invention is furthermore not restricted to human diseases and can be used for mammals, as for example bovines, pigs, horses, cats, dogs, rodents, such as rat, mouse, goats, and other domestic animals or animals in danger of extinction due to a cancerous disease such as, for example, the Tasmanian devil.

1. HLA ligands from the malignant and healthy tissue were identified and differentially quantified by label-free liquid chromatography-coupled mass spectrometry (LCMS) in order to determine over-presented TUMAPs (tumor-associated peptides).

2. Genome-wide messenger ribonucleic acid (mRNA) expression analysis by microarrays was used to identify genes over-expressed in the malignant tissue compared with a range of normal organs and tissues.

3. Identified HLA ligands were compared to gene expression data. Over-presented TUMAPs encoded by selectively expressed or over-expressed genes as detected in step 2 were considered suitable TUMAP candidates for a multi-peptide vaccine.

4. Literature research was performed in order to identify additional evidence supporting the relevance of the identified peptides as TUMAPs and exclude the possibility of the protein playing a crucial role in another pathway.

5. Peripheral T cells from blood of healthy individuals were tested for reactivity against the TUMAP candidates using several immunoassays (in vitro T-cell assays).

Figure 10:
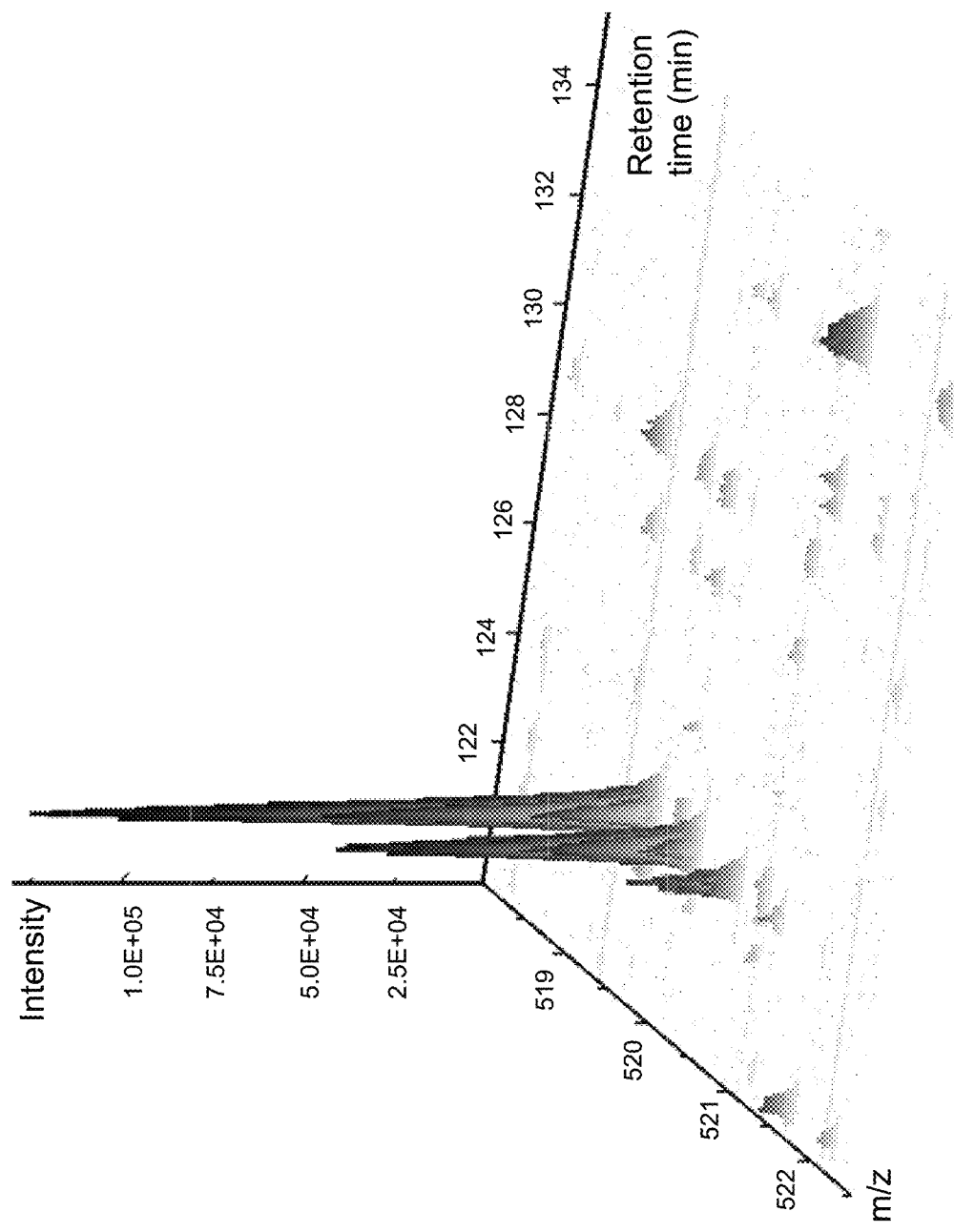

FIG. 10: shows a partial LCMS map plotted by OpenMS (M. Sturm and O. Kohlbacher. TOPPView: an open-source viewer for mass spectrometry data. *J Proteome. Res* 8 (7):3760-3763, 2009) with signal for peptide YLLPAIVHI at 122 min.

DETAILED DESCRIPTION OF THE INVENTION

The term "presentation profile" or "presentation plot" as used herein shows the average presentation for a peptide in distinct samples visualized in a bar chart. The presentation is expressed in percent as abundance relative to the maximum area. The variation is visualized as 95% confidence intervals based on the measured replicates. If the peptide was identified in a sample but no quantification was possible, it is indicated by the label NA (not available/no area).

The "presentation score" is a measure of peptide over-presentation in one group of tissues as compared to another group with values between 0 and 1. The smaller the presentation score, the more likely the overpresentation. If a peptide was not found on any normal or non-diseased samples, no score can be calculated and is therefore set to zero.

To determine a set of significantly overpresented TUMAPs, one has to choose a significance threshold (e.g. 0.05) and include/get all TUMAPs with presentation score smaller than this threshold. Thus, the presentation score reflects the probability of a TUMAP appearing overpresented by chance.

Statistically, the presentation score may be the p-value of a linear mixed model. In this case, the score models the presentation data (TUMAP feature areas) incorporating the variation between and within samples as random effects and the difference between a e.g. tumor entity and normal tissues as fixed effect. In a more simplified approach, the presentation score may be the p-value of a t-test.

The presentation score is adjusted for multiple testing using FDR (false discovery rate).

The term "quality control" as used herein relates to verifying that the data as used in the present method meets sufficient criteria in order to allow for it to be used in the present method. One example is the total number of identified sequences and the number of sequences with small variance in areas based on peptide quantity reproducibility for every sample as analyzed, that is, how many peptide sequences can be identified (preferably reliably identified) in a sample and which percentage of those identified peptides (such as, for example, 25%, 30%, 50% or even 75%) can be assigned with a reliable area with small variance (e.g. CV of 20% or less). This is a prerequisite for reliable normalization between different samples. Usually, the higher the number of peptide sequences that can be reliably identified the "better" the quality of the data. Another example is controlling the quality of identifications and area estimates, for example by "classical" visual inspection of the peptide identification results and of the area reproducibilities, or by statistical analysis.

In a first aspect of the present invention, the object of the invention is solved by a method for the identification and label-free quantification of MHC ligand peptides on primary tissue samples from at least one mammal, comprising a) providing at least one diseased primary tissue sample and at least one sample of primary healthy tissue preferably corresponding to the diseased tissue, b) isolating MHC ligand peptides from said sample(s), c) performing an HPLC-MS analysis on said MHC ligand peptides, d) extracting the precursor ion signal intensity (area) for each signal, as derived from step c), e) identifying the sequences of said MHC ligand peptides by fragment spectra clustering and database search, in order to group areas between different runs and samples, and normalizing areas within replicate runs to compensate technical performance/sensitivity differences between replicate runs resulting in average quantities for each peptide per sample including error estimates, f) assigning of said sequences to MHC alleles in order to generate allele-specific sequence subgroups for a comparison between different samples, and normalizing between different samples using the allele-specific subgroups to account for different sample sizes or MHC expression levels: result is relative quantities comparable between samples, g) performing a data quality control based on peptide reproducibility for every sample, verifying that the total number of identified sequences and the number of sequences with small variance in areas is as high as possible, h) calculating presentation profiles and scores in order to determine a potential over-presentation of MHC ligand peptides, i) controlling the quality of identifications and area estimates, for example by visual inspection of the peptide identification results and of the area reproducibilites, or statistical analysis, j) comparing the values detected in said at least one diseased primary tissue sample with the value(s) obtained from said at least one primary healthy tissues, and k) quantifying said MHC ligand peptides In a second aspect of the present invention, the object of the invention is solved by a method for identifying and quantifying MHC ligand peptides on primary tissue samples, comprising a) providing at least one diseased tissue sample and at least one sample of healthy tissue preferably corresponding to the diseased tissue from at least one mammal, b) isolating MHC ligand peptides from said sample(s), c) performing a HPLC-MS analysis on said MHC ligand peptides, d) extracting the precursor ion signal intensity (area) for each signal, as derived from step c), e) identifying the sequences of said MHC ligand peptides by fragment spectra clustering and database search, in order to group areas between different runs and samples, and normalizing areas within replicate runs to compensate technical performance/sensitivity differences between replicate runs resulting in average quantities for each peptide per sample including error estimates, f) assigning of said sequences to MHC alleles in order to generate allele-specific sequence subgroups for a comparison between different samples, and normalizing between different samples using the allele-specific subgroups to account for different sample sizes or MHC expression levels: result is relative quantities comparable between samples, g) performing a data quality control based on peptide reproducibility, verifying that the total number of identified sequences and the number of sequences with small variance in area is at least 25, preferably 50, and more preferably 100, h) calculating presentation profiles and scores in order to determine a potential over-presentation of MHC ligand peptides, i) controlling the quality of identifications and area estimates by statistical analysis, j) comparing the values detected in said at least one diseased primary tissue sample with the value(s) obtained from said at least one healthy tissues, and k) quantifying said MHC ligand peptides.

Preferred is a method according to the present invention, wherein the total number of identified sequences and the number of sequences with small variance in areas is not significantly lower (e.g. less 20%, such as 10% or even 1%) than in the other samples included in the quantitative comparative analysis.

Preferred is a method according to the present invention, wherein said MHC ligand peptide is selected from a tumor associated peptide (TAA) or disease associated peptide (DAA).

Further preferred is a method according to the present invention that further comprises a selection of overrepresented and/or tumor-specific MHC ligand peptides.

Even further preferred is a method according to the present invention, wherein said diseased sample is a tumor sample or a sample of infected tissue. In the context of the present invention, samples that are directly derived from subjects, such as patients, are termed "primary" samples, such as primary tissue or tumor samples, in contrast to samples of cell lines, such as, for example, established tumor cell lines. The samples can be fresh or conserved (e.g. frozen or prepared), as long as they are suitable for the method according to the invention.

As a preferred example, the HLA peptide pools from shock-frozen (primary) tissue samples can be obtained by immune precipitation from solid tissues using for example the HLA-A, -B, -C-specific antibody w6/32 or the HLA-A*02-specific antibody BB7.2 coupled to CNBr-activated sepharose, followed by acid treatment, and ultrafiltration. For different HLA-alleles other specific antibodies known in the art can be used as there are for example GAP-A3 for A*03, B1.23.2 for B-alleles. There are corresponding methods to obtain MHC-class I peptides for other mammals that are well known in the art.

The method according to the invention can also be used in the context of infectious diseases, such as viral or bacterial infections, for example dengue fever, Ebola, Marburg virus, tuberculosis (TB), meningitis or syphilis, preferable the method is used on antibiotic-resistant strains of infectious organisms, autoimmune diseases, such as arthritis, parasitic infections, such as malaria and other diseases such as MS and Morbus Parkinson, as long as the immune answer is a MHC class I answer.

Table 1 shows preferred examples for parasitic infections of humans:

| | | Protozoan organisms | | |
|---|---|---|---|---|
| Common name of organism or disease | Latin name | Body parts affected | Prevalence | Source/Transmission (Reservoir/Vector) |
| Babesiosis | *Babesia* *B. divergens, B. bigemina, B. equi, B. microfti, B. duncani* | red blood cells | New York, Martha's Vineyard, Nantucket (different species have worldwide distribution) | tick bites |
| Balantidiasis | *Balantidium coli* | intestinal mucosa | | |
| Blastocystosis | *Blastocystis* | intestinal | 2-20% of population | eating food contaminated with feces from an infected human or animal |
| Coccidia | *Cryptosporidium* | intestines | widespread | |
| Dientamoebiasis | *Dientamoeba fragilis* | intestines | up to 10% in industrialized countries | ingesting water or food contaminated with feces |

-continued

| | | Protozoan organisms | | |
|---|---|---|---|---|
| Amoebiasis | *Entamoeba histolytica* | Intestines | areas with poor sanitation, high population density and tropical regions | fecal-oral transmission |
| Giardia | *Giardia lamblia* | lumen of the small intestine | widespread | ingestion of dormant cysts in fecal contaminated water or food |
| Isosporiasis | *Isospora belli* | epithelial cells of small intestines | worldwide - less common than *Toxoplasma* or *Cryptosporidium* | fecal oral route |
| Leishmaniasis | *Leishmania* | cutaneous, mucocutaneous, or visceral | Visceral leishmaniasis- Worldwide; Cutaneous leishmaniasis - Old World; Mucocutaneous leishmaniasis - New World | *Phlebotomus* - bite of several species of nocturnal *phlebotomus* sandflies |
| Primary amoebic meningoencephalitis | *Naegleria fowleri* | brain | rare but deadly | Nasal insufflation of contaminated warm fresh water, poorly chlorinated swimming pools, hot springs, soil |
| Malaria | *Plasmodium falciparum* (80% of cases), *Plasmodium vivax*, *Plasmodium ovale*, *Plasmodium malariae* | red blood cells | tropical - 250 million cases/year | *Anopheles* mosquito, bites at night |
| Rhinosporidiosis | *Rhinosporidium seeberi* | nose, nasopharynx | India and Sri Lanka | nasal mucosa came into contact with infected material through bathing in common ponds |
| Toxoplasmosis - Parasitic pneumonia | *Toxoplasma gondii* | eyes, brain, heart, liver | widespread - up to one third of all humans | ingestion of uncooked/undercooked pork/lamb/goat with *Toxoplasma bradyzoites*, ingestion of raw milk with *Toxoplasma tachyzoites*, ingestion of contaminated water food or soil with oocysts in cat feces that is more than one day old |
| Trichomoniasis | *Trichomonas vaginalis* | female urogenital tract (males asymptomatic) | 7.4 million Americans | sexually transmitted infection |
| Sleeping sickness | *Trypanosoma brucei* | blood lymph and central nervous systems | 50,000 to 70,000 people | tsetse fly, bites at night |
| Chagas disease | *Trypanosoma cruzi* | colon, esophagus, heart, nerves, muscle and blood | Mexico, Central America, South America - 16-18 million | *Triatoma*/Red *uviidae* - Insect Vector, bites at night |

| | | Helminths organisms (worms) | | |
|---|---|---|---|---|
| Common name of organism or disease | Latin name | Body parts affected | Prevalence | Transmission/Vector |
| Ancylostomiasis/ Hookworm | *Ancylostoma duodenale*, *Necator americanus* | lungs, small intestine, blood | common in tropical, warm, moist climates | penetration of skin by L3 larva |
| Anisakiasis | *Anisakis* | allergic reaction | incidental host | ingestion of raw fish, squid, cuttlefish, octopus |
| Roundworm - Parasitic pneumonia | *Ascaris* sp. *Ascaris lumbricoides* | Intestines, liver, appendix, pancreas, lungs, Löffler's syndrome | common in tropical and subtropical regions | |
| Roundworm | *Baylisascaris* *Baylisascaris procyonis*, *Baylisascaris melis*, *Baylisascaris transfuga*, *Baylisascaris columnaris*, *Baylisascaris devosi*, *Baylisascaris laevis* | | | depending on species: ingestion of material contaminated by stool from raccoons, badgers, bears, otters, martens |
| | *Brugia malayi*, *Brugia timori* | lymph nodes | tropical regions of Asia | Arthropods |
| Tapeworm - Tapeworm infection | *Cestoda* | intestine | rare | |
| Clonorchiasis | *Clonorchis sinensis*; *Clonorchis viverrini* | | | |
| | *Dicrocoelium dendriticum* | gall bladder | rare | ingestion of ants |

-continued

| | Protozoan organisms | | | |
|---|---|---|---|---|
| Dioctophyme renalis infection | *Dioctophyme renale* | kidneys (typically the right) | Worldwide | Ingestion of undercooked or raw freshwater fish |
| Diphyllobothriasis - tapeworm | *Diphyllobothrium latum* | intestines, blood | Europe, Japan, Uganda, Peru, Chile | ingestion of raw fresh water fish |
| Guinea worm - Dracunculiasis | *Dracunculus medinensis* | subcutaneous tissues, muscle | Sudan | |
| Echinococcosis - tapeworm | *Echinococcus granulosus*, *Echinococcus multilocularis*, *E. vogeli*, *E. oligarthrus* | liver, lungs, kidney, spleen | Mediterranean countries | as intermediate host, ingestion of material contaminated by feces from a carnivore; as definite host, ingestion of uncooked meat (offal) from a herbivore |
| | *Echinostoma echinatum* | small intestine | Far East | ingestion of raw fish, mollusks, snails |
| Pinworm - Enterobiasis | *Enterobius vermicularis*, *Enterobius gregorii* | intestines, anus | widespread; temperate regions | |
| Liver fluke - Fasciolosis | *Fasciola hepatica*, *Fasciola gigantica* | liver, gall blader | *Fasciola hepatica* in Europe, Africa, Australia, the Americas and Oceania; *Fasciola gigantica* only in Africa and Asia, 2.4 million people infected by both species | freshwater snails |
| Fasciolpsiasis - intestinal fluke | *Fasciolopsis buski* | intestines | East Asia - 10 million people | ingestion of infested water plants or water (intermediate host: amphibic snails) |
| Gnathostomiasis | *Gnathostoma spinigerum*, *Gnathostoma hispidum* | subcutaneous tissues (under the skin) | rare - Southeast Asia | ingestion of raw or undercooked meat (eg, freshwater fish, chicken, snails, frogs, pigs) or contaminated water |
| Hymenolepiasis | *Hymenolepis nana*, *Hymenolepis diminuta* | | | ingestion of material contaminated by flour beetles, meal worms, cockroaches |
| Loa loa filariasis, Calabar swellings | *Loa loa filaria* | Connective tissue, lungs, eye | rain forest of West Africa - 12-13 million people | *Tabanidae* - horse fly, bites in the day |
| Mansonelliasis, Filariasis | *Mansonella streptocerca* | subcutaneous layer of skin | | insect |
| Metagonimiasis - intestinal fluke | *Metagonimus yokogawai* | | Siberia, Manchuria, Balkan states, Israel, Spain | ingestion of undercooked or salted fish |
| River blindness | *Onchocerca volvulus*, Onchocerciasis | skin, eye, tissue | Africa, Yemen, Central and South America near cool, fast flowing rivers | *Simulium*/Black fly, bite during the day |
| Chinese Liver Fluke | *Opisthorchis viverrini*, *Opisthorchis felineus*, *Clonorchis sinensis* | bile duct | 1.5 million people in Russia | consuming infected raw, slightly salted or frozen fish |
| Paragonimiasis, Lung Fluke | *Paragonimus westermani*; *Paragonimus africanus*; *Paragonimus caliensis*; *Paragonimus kellicotti*; *Paragonimus skrjabini*; *Paragonimus uterobilateralis* | lungs | East Asia | ingestion of raw or undercooked freshwater crabs crayfishes or other crustaceans |
| Schistosomiasis - bilharzia, bilharziosis or snail fever (all types) | *Schistosoma* sp. | | Africa, Caribbean, eastern South America, east Asia, Middle East - 200 million people | skin exposure to water contaminated with infected fresh water snails |
| intestinal schistosomiasis | *Schistosoma mansoni* | intestine, liver, spleen, lungs, skin | Africa, Caribbean, South America, Asia, Middle East - 83 million people | skin exposure to water contaminated with infected *Biomphalaria* fresh water snails |
| urinary schistosomiasis | *Schistosoma haematobium* | kidney, bladder, ureters, lungs, skin | Africa, Middle East | skin exposure to water contaminated with infected *Bulinus* sp. snails |
| Schistosomiasis by *Schistosoma japonicum* | *Schistosoma japonicum* | intestine, liver, spleen, lungs, skin | China, East Asia, Philippines | skin exposure to water contaminated with infected *Oncomelania* sp. snails |
| Asian intestinal schistosomiasis | *Schistosoma mekongi* - | | South East Asia | skin exposure to water contaminated with infected *Neotricula aperta* - fresh water snails |
| Sparganosis | *Spirometra erinaceieuropaei* | | | ingestion of material contaminated with infected dog or cat feces (humans: dead-end host) |
| Strongyloidiasis - Parasitic pneumonia | *Strongyloides stercoralis* | Intestines, lungs, skin (Larva currens) | | skin penetration |
| Beef tapeworm | *Taenia saginata* | Intestines | worldwide distribution | ingestion of undercooked beef |
| Pork tapeworm | *Taenia solium* | | | ingestion of undercooked pork |
| Toxocariasis | *Toxocara canis*, *Toxocara cati* | liver, brain, eyes (*Toxocara canis* - Visceral larva *migrans*, Ocular larva *migrans*) | worldwide distribution | pica, unwashed food contaminated with *Toxocara* eggs, undercooked livers of chicken |

-continued

| Protozoan organisms | | | | |
|---|---|---|---|---|
| Trichinosis | *Trichinella spiralis, Trichinella britovi, Trichinella nelsoni, Trichinella nativa* | muscle, periorbital region, small intestine | more common in developing countries due to improved feeding practices in developed countries. | ingestion of undercooked pork |
| Swimmer's itch | *Trichobilharzia regenti, Schistosomatidae* | | | skin exposure to contaminated water (snails and vertebrates) |
| Whipworm | *Trichuris trichiura, Trichuris vulpis* | large intestine, anus | common worldwide | accidental ingestion of eggs in dry goods such as beans, rice, and various grains or soil contaminated with human feces |
| ElephantiasisLymphatic filariasis | *Wuchereria bancrofti* | lymphatic system | Tropical and subtropical | mosquito, bites at night |

| Other organisms | | | | |
|---|---|---|---|---|
| Common name of organism or disease | Latin name (sorted) | Body parts affected | Prevalence | Transmission/Vector |
| parasitic worm Halzoun Syndrome | *Archiacanthoc ephala Linguatula serrata* | nasopharynx | Mid East | ingestion of raw or undercooked lymph nodes (eg, meat from infected camels and buffalos) |
| Myiasis | *Oestroidea, Calliphoridae, Sarcophagidae* | dead or living tissue | | |
| Human Botfly | *Dermatobia hominis* | Subcutaneous tissue | Central and South America | Mosquitoes and biting flies |
| Candiru | *Trichomycteridae* | Urethra | Amazon River Basin | Urinating in waters inhabited by the fish without proper protection |

Examples for autoimmune diseases (including diseases not officially declared to be autoimmune diseases) are Chronic obstructive pulmonary disease, Ankylosing Spondylitis, Crohn's Disease (one of two types of idiopathic inflammatory bowel disease "IBD"), Dermatomyositis, Diabetes mellitus type 1, Endometriosis, Goodpasture's syndrome, Graves' disease, Guillain-Barre syndrome (GBS), Hashimoto's disease, Hidradenitis suppurativa, Kawasaki disease, IgA nephropathy, Idiopathic thrombocytopenic purpura, Interstitial cystitis, Lupus erythematosus, Mixed Connective Tissue Disease, Morphea, Myasthenia gravis, Narcolepsy, Neuromyotonia, Pemphigus vulgaris, Pernicious anaemia, Psoriasis, Psoriatic Arthritis, Polymyositis, Primary biliary cirrhosis, Relapsing polychondritis, Rheumatoid arthritis, Schizophrenia, Scleroderma, Sjogren's syndrome, Stiff person syndrome, Temporal arteritis (also known as "giant cell arteritis"), Ulcerative Colitis (one of two types of idiopathic inflammatory bowel disease "IBD"), Vasculitis, Vitiligo and Wegener's granulomatosis.

The present invention is not restricted to human diseases, but can be used for mammals, for example cows, pigs, horses—preferably racing horses, cats, dogs, rodents, such as rat, mouse, goat, and other domestic animals or mammals in danger of extinction due to a cancerous disease as for example the Tasmanian devil.

In yet another preferred embodiment of the method according to the present invention, the controlling of the quality, at least in part, comprises the use an automate and/or manual or visual inspection.

Yet another preferred embodiment of the method according to the present invention further comprises at least one step selected from the group of in step d) aligning the retention time to assign corresponding signals within replicate runs without a knowledge about the sequences, and/or assigning the corresponding signals between different samples by retention time alignment without a knowledge about the sequences, in step h) implementing relative presentation data from more than one peptide per gene to calculate a gene-centered over-presentation score, and in step i) performing an quality control based on spiked peptides.

Most preferably, the method according to the present invention is performed in vitro.

In still another preferred embodiment of the method according to the present invention, the steps of said method are performed in the order as indicated in the claim or as above. In still another preferred method according to the present invention said method consists of the steps as indicated above and herein.

In a further preferred aspect of the method according to the present invention, said method further comprises the step of synthesizing said at least one MHC ligand peptide as identified and/or quantified by said method on a synthesizer or manually.

Preferred is a method according to the present invention that further comprises the step of testing said MHC ligand peptide as a synthesized peptide or purified peptide for its immunogenicity. Respective methods are known to the person of skill and described both in the respective literature and herein.

In a further preferred aspect of the method according to the present invention, said method relates to personalized therapy and diagnosis. For this, said sample(s) as analyzed is/are derived from one individual. Also, a personalized MHC ligand profile, preferably a personalized disease-specific MHC ligand profile, based on said MHC ligand peptides as identified and/or quantified can be generated based on the method according to the present invention as described herein.

In a further preferred aspect of the method according to the present invention, said total number of identified sequences and the number of sequences with small variances in areas is higher than 5, preferably higher than 25, more preferably higher than 50, and most preferred higher than 100.

Surprisingly, in the context of the present invention the inventors found that by combining an expression analysis with the quantification of antigenic tumor peptides that have been isolated and analyzed, specific candidates for an individual vaccine can be readily identified. For the first time, this new approach as provided by the inventors allows for the identification and selection of relevant over-presented peptide vaccine candidates based on a direct relative quantitation of MHC-, preferably HLA-restricted, peptide levels on cancer or other infected tissues in comparison to several different non-cancerous tissues or no-infected tissues and organs. This was achieved by the development of label-free differential quantitation using liquid chromatography-coupled mass spectrometry data processed by a proprietary data analysis pipeline, combining algorithms for sequence identification, spectral clustering, ion counting, and normalization. The approach can be applied to peptides from any HLA class I allele, and routine quantitation has already been performed for two very common alleles and several different tumor entities as an example. Extensive validation experiments confirmed the accuracy of our results. The normalization strategy was corroborated by measurements of beta-2 microglobulin levels in affinity chromatography elutions by western blotting.

Commonly used "reverse immunology" approaches, which are based on prediction algorithms to select HLA-binding peptides out of a protein sequence are hampered by the problem that these approaches neglect the important step of antigen processing. Most of the peptides selected this way are not presented physiologically on cells of primary tissues or cell lines because they bind to HLA but are not processed from the protein.

In another preferred embodiment of the method according to the present inventions, said method is label-free, i.e. does exclude the use of labels, in particular chemical labels, for example for the peptides to be analyzed.

In yet another preferred embodiment of the method according to the present invention, said method does furthermore exclude the use of knock-out cells, cell lines or animals.

In one further preferred aspect of the method according to the invention, the isolated MHC/HLA ligands are separated according to their hydrophobicity by reversed-phase chromatography (e.g. nanoAcquity UPLC system, Waters) followed by detection in an LTQ-Orbitrap hybrid mass spectrometer (ThermoElectron). Each sample is analyzed label-free by acquisition of five replicate LCMS runs. The LCMS data is processed by analyzing the LCMS survey as well as the Tandem-MS (MS/MS) data. The data analysis is optimized to handle incremental and replicated sample acquisition.

The tandem-MS spectra as generated were extracted using msn_extract (ThermoScientific) and searched with Sequest against a protein database such as the IPI database. The protein database hits were subsequently validated by automated quality filtering using thresholds optimized for HLA peptidomics data.

For increased identification sensitivity, an in-house developed spectral clustering algorithm was used to assign spectra to known peptide MS/MS which are being collected in the IFL (Immatics Fragment spectra Library). The MS/MS scans of a new LCMS run were added incrementally to the IFL scan by scan. The clustering uses a growing k-means clustering algorithm adapted for spectral data.

Due to the sequence identification and fragment spectra clustering, it is then possible to group intensity values (areas) for the same sequence or cluster from different runs and samples.

Comparability of peptide groups restricted to the same HLA allele between different samples is possible based on a common allele-specific antibody used for purification if available or alternatively based on assignment of sequences to common HLA-alleles by means of anchor amino acid patterns.

Each new data set is integrated in a database (for example MySQL) and cross-referenced to available proteomic, genomic and literature data.

LCMS survey data is analyzed independently using ion counting and making use of the high-mass accuracy. To extract LCMS signals as well as the integrated signal areas a feature finding algorithms for example implemented by the program SuperHirn (L. N. Mueller, O. Rinner, A. Schmidt, S. Letarte, B. Bodenmiller, M. Y. Brusniak, O. Vitek, R. Aebersold, and M. Muller. SuperHirn—a novel tool for high resolution LC-MS-based peptide/protein profiling. *Proteomics*. 7 (19):3470-3480, 2007.) can be used.

Combining both data sets yields quantitative data for each identified peptide, which can subsequently be normalized in a two-tier approach based on central tendency normalization to account for variation between technical replicates (LC-MS runs) and between samples of different tissue origin such as tumor and healthy tissues (see above). The latter differences can be, for example, due to or derived from different MHC expression levels or different amounts of starting materials.

For utmost reliability, in a preferred embodiment, only peptides, which have a coefficient of variation (CV) of smaller than 25%, preferably 20%) between their replicate areas, are considered in the first normalization step.

To extract over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (J. Pinheiro, D. Bates, S. DebRoy, Sarkar D., R Core team. nlme: Linear and Nonlinear Mixed Effects Models. 2008) adjusting for multiple testing by False Discovery Rate (Y. Benjamini and Y. Hochberg. Controlling the False Discovery Rate: A Practical and Powerful Approach to Multiple Testing. *Journal of the Royal Statistical Society. Series B (Methodological)*, Vol. 57 (No. 1):289-300, 1995).

Sequence assignment and areas for peptides selected as potential vaccine candidates are confirmed by manual inspection.

A further preferred optional step of the present invention is the alignment of retention times between replicate LC-MS runs to avoid the requirement for sequence assignment to signals for the first normalization step.

A further preferred optional step of the present invention is the alignment of retention times between different samples to avoid the requirement for sequence assignment to signals for the second normalization step.

A further preferred optional step of the present invention is the calculation of a gene-centered over-presentation score by combination of single peptide over-presentation scores if more than one peptide is identified from the same gene.

A further preferred optional step of the present invention is an automatic quality control of replicate normalization based on molecules spiked into the samples in defined amounts.

By isolating antigenic peptides and matching them with gene expression and presentation on the cells leading to profiles of tumorous tissue, it can be avoided that a vast number of possible immunoreactive peptides is obtained. Rather, specific peptides are identified according to the present invention, which are actually presented by MHC-molecules and which are thus suitable as immunoreactive peptides.

With the method according to the invention it is furthermore possible to identify patient-specific peptides, i.e. it is possible to precisely match peptides, which are to be used as vaccine, to the patient in order to induce a specific immune response.

For example, industrial laboratories—after having received patient samples—can systematically and efficiently perform the present method, and can—after having identified suitable immunoreactive peptides—provide clinics in charge with the peptide sequences; the clinics can then synthesize and administer the peptides. Nevertheless, it is also possible that a laboratory is carrying out identification as well as production of the peptides suitable for the respective patient.

Therefore, the new method of the present invention is applicable within the scope of a mere service as well as in combination with the supply of the identified immunoreactive peptide.

Further aspects of the invention are immunoreactive peptides, which are identified and/or prepared by the method according to the invention. After identification these peptides can be selectively and specifically prepared for the treatment of the patient.

Another aspects of the invention then relates to a pharmaceutical composition comprising one or more peptides that have been identified and/or prepared by the method according to the invention.

The composition may be applied, for example, parenterally, for example subcutaneously, intradermally or intramuscularly, or may be administered orally, depending on the formulation and the target disease. In doing so, the peptides are dissolved or suspended in a pharmaceutically acceptable carrier, preferably an aqueous carrier; the composition can further comprise additives, for example buffers, binders, etc. The peptides can also be administered together with immunostimulating substances, for example cytokines According to one aspect of the invention, the peptides may be used for the treatment of tumorous diseases and for preparing a drug for treatment of tumor diseases.

Tumorous diseases to be treated comprise solid tumors, such as renal, breast, pancreas, gastric, testis and/or skin cancer or blood cancers such as AML. This list of tumor diseases is only exemplary, and is not intended to limit the area of application.

The peptides can further be used for assessment of the therapy-course of a tumor disease.

The peptides can also be used for monitoring a therapy in other immunizations or therapies. Therefore, the peptide may not only be used therapeutically but also diagnostically.

A further aspect of the invention then relates to the use of the peptides for generating an antibody. Polyclonal antibodies can be obtained, in a general manner, by immunization of animals by means of injection of the peptides and subsequent purification of the immunoglobulin. Monoclonal antibodies can be generated according to standardized protocols known in the art.

Further aspects of the invention are nucleic acid molecules encoding for the peptide isolated with the method according to the invention. The nucleic acid molecules can be DNA- or RNA-molecules and can be used for immune therapy of cancer as well. According to one aspect of the invention the nucleic acid molecules can be provided in a vector, such as, for example, an expression vector.

A further aspect of the invention relates to a cell that is genetically modified by means of the nucleic acid molecule (e.g. in an expression vector), such, that the cell is producing a peptide identified according to the invention.

Another aspect of the invention relates to a method for preparing an immunoreactive peptide with which a peptide is identified according to the disclosed method and the identified peptide is synthesized chemically, in vitro or in vivo. Peptides can be prepared by chemical linkage of amino acids by the standard methods known in the art.

Peptides can be prepared in vitro, for example, in cell-free systems, and in vivo using cells. The peptides can be formulated as disclosed, for example, in EP2111867 by Lewandrowski et al.

Yet a further aspect relates to the method according to the invention comprising a further step in which the reactivity of peripheral leukocytes, preferably of T-leukocytes, against the isolated antigenic peptides, is tested.

A further aspect relates to the method according to the invention, wherein the reactivity of peripheral leukocytes against the isolated antigenic peptides is tested by means of measuring γ-Interferon-mRNA and/or cytokin-mRNA synthesised by the leukocytes.

By detecting γ-Interferon- or cytokin-mRNA it is possible to precisely prove the specific reactivity of leukocytes, preferably of T-lymphocytes against antigenic peptides. Both substances are secreted by activated T-lymphocytes after their activation by corresponding antigenic peptides.

Yet another aspect relates to the method according to the invention, wherein a further step is performed, in which the presence of the T-lymphocytes is detected. Using this method, it is possible to specifically detect to what extent T-lymphocytes directed against isolated and identified peptides are pre-existing in patients. By performing this step it is possible to apply, as a vaccine, only those peptides against which T-lymphocytes are already pre-existing in the patient. The peptides can then be used to activate these specific T-lymphocytes.

A further aspect relates to the method according to the invention, wherein the detection of specific pre-existing T-lymphocytes is performed by labelling the leukocytes with reconstituted complexes of antigen-presenting molecules and antigenic peptide.

More than 11,000 different peptides have been quantified on 70 cancer and 40 non-cancerous samples by the inventors so far. Significance scores for over-presentation within individual cancer entities as well as average presentation levels including confidence intervals for every single peptide and sample were established. Peptides exclusively presented on tumor tissue and peptides over-presented in tumor versus non-cancerous tissues and organs have been identified.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 14 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response.

A T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans, there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*024 are examples of different MHC class I alleles that can be expressed from these loci.

Immunotherapeutic Approaches for Treatment

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defenses against cancer. CD8-positive T-cells in particular, which recognize class I molecules of the major histocompatibility complex (MHC)-bearing peptides of usually 8 to 12 residues derived from proteins or defect ribosomal products (DRIPS) located in the cytosols, play an important role in this response. The MHC-molecules of the human are also designated as human leukocyte-antigens (HLA).

MHC class I molecules can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature.

For proteins to be recognized by cytotoxic T-lymphocytes as tumor-specific or -associated antigens, and to be used in a therapy, particular prerequisites must be fulfilled. The antigen should be expressed mainly by tumor cells and not by normal healthy tissues or in comparably small amounts. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or apoptosis. Additionally, also downstream targets of the proteins directly causative for a transformation may be upregulated and thus be indirectly tumor-associated. Such indirectly tumor-associated antigens may also be targets of a vaccination approach. Essential is in both cases the presence of epitopes in the amino acid sequence of the antigen, since such peptide ("immunogenic peptide") that is derived from a tumor associated or disease associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope. Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues (Lemmel et al. 450-54; Weinschenk et al. 5818-27). However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell that upon stimulation with a specific antigen can be clonally expanded and is able to execute effector functions ("effector T cell").

T-helper cells play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

Since both types of response, CD8 and CD4 dependent, contribute jointly and synergistically to the anti-tumor effect, the identification and characterization of tumor-associated antigens recognized by either CD8+ CTLs (MHC class I molecule) or by CD4-positive CTLs (MHC class II molecule) is important in the development of tumor vaccines. It is therefore an object of the present invention, to provide compositions of peptides that contain peptides binding to MHC complexes of either class.

Considering the severe side-effects and expenses associated with treating cancer better prognosis and diagnostic methods are desperately needed. Therefore, there is a need to identify other factors representing biomarkers for cancer in general and gastric cancer in particular. Furthermore, there is a need to identify factors that can be used in the treatment of cancer in general and gastric cancer in particular.

Furthermore there is no established therapeutic design for gastric cancer patients with biochemical relapse after radical prostatectomy, usually caused by residual tumor left in situ in the presence of locally advanced tumor growth. New therapeutic approaches that confer lower morbidity with comparable therapeutic efficacy relative to the currently available therapeutic approaches would be desirable.

The present invention provides peptides that are useful in treating gastric cancer and other tumors that over-present the peptides of the invention. These peptides were shown by mass spectrometry to be naturally presented by HLA molecules on primary human gastric cancer samples (see Example 1 and FIG. 1).

The source gene from which the peptides are derived were shown to be highly over-expressed in gastric cancer, renal cell carcinoma, colon cancer, non-small cell lung carcinoma, adenocarcinoma, prostate cancer, benign neoplasm and malignant melanoma compared with normal tissues (see Example 2 and FIG. 2) demonstrating a high degree of tumor association of the peptide, i.e. these peptides are strongly presented on tumor tissue but not on normal tissues.

MHC/HLA-bound peptides can be recognized by the immune system, specifically T lymphocytes/T cells. T cells can destroy the cells presenting the recognized MHC- or HLA-peptide complex, e.g. gastric cancer cells presenting the derived peptides.

The invention shall now be described further in the following examples, nevertheless, without being limited thereto. In the accompanying Figures and the Sequence Listing, FIG. 1: shows an exemplary mass spectrum from CDC2-001 demonstrating its presentation on primary tumor sample GC2464. NanoESI-LCMS was performed on a peptide pool eluted from the GC sample 2464. The mass chromatogram for m/z 597.3501±0.001 Da, z=2 shows a peptide peak at the retention time 151.63 min. B) The detected peak in the mass chromatogram at 151.63 min revealed a signal of m/z 597.3501 in the MS spectrum. C) A collisionally induced decay mass spectrum from the selected precursor m/z 597.3501 recorded in the nanoESI-LCMS experiment at the given retention time confirmed the presence of CDC2-001 in the GC2464 tumor sample. D) The fragmentation pattern of the synthetic CDC2-001 reference peptide was recorded and compared to the generated natural TUMAP fragmentation pattern shown in C for sequence verification.

Figure 2:
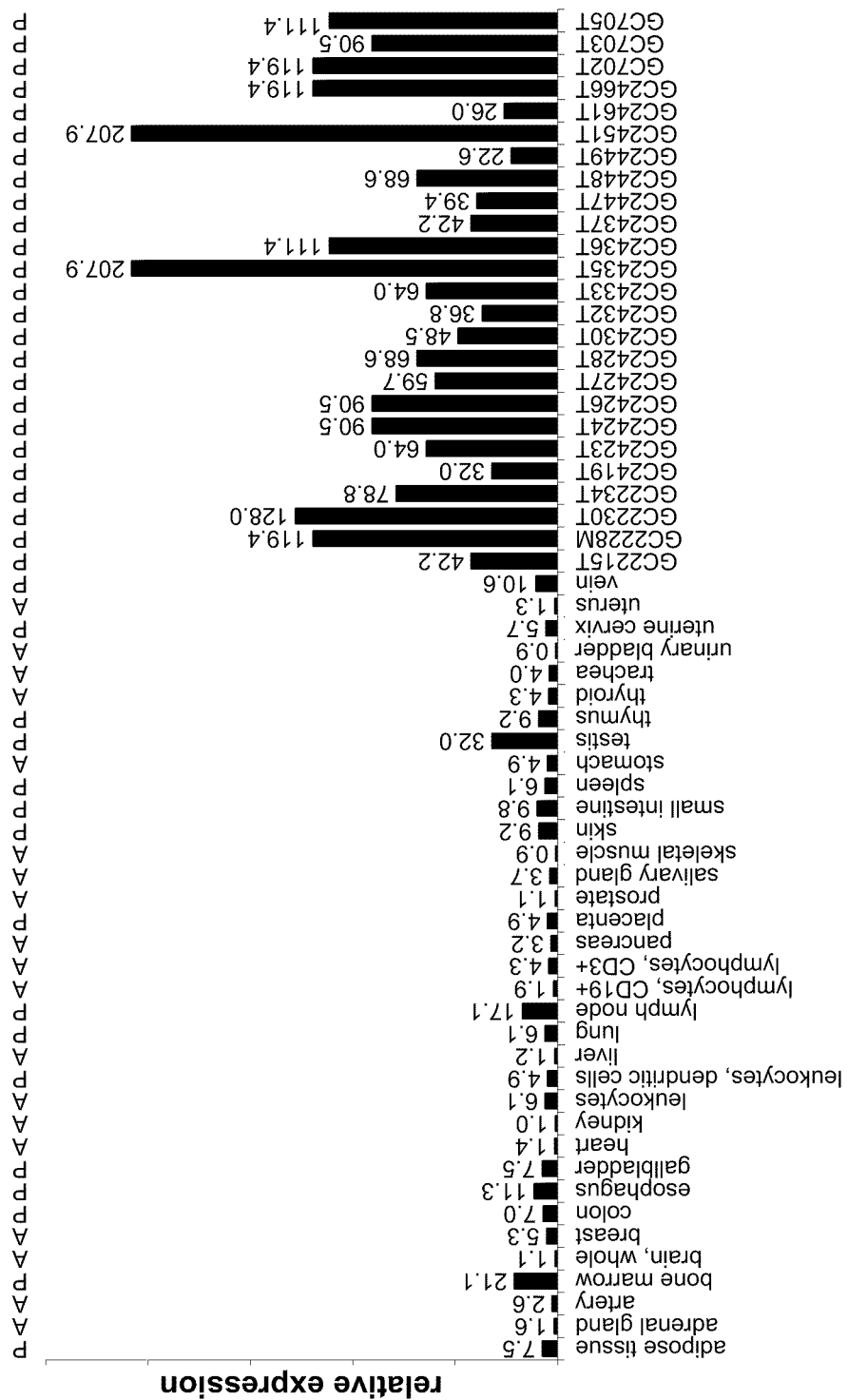
FIG. 2: shows expression profiles of mRNA of selected proteins in normal tissues and in 25 gastric cancer samples; CDC2 (Probeset ID: 203213_at); ASPM (Probeset ID: 219918_s_at).
Figure 2:
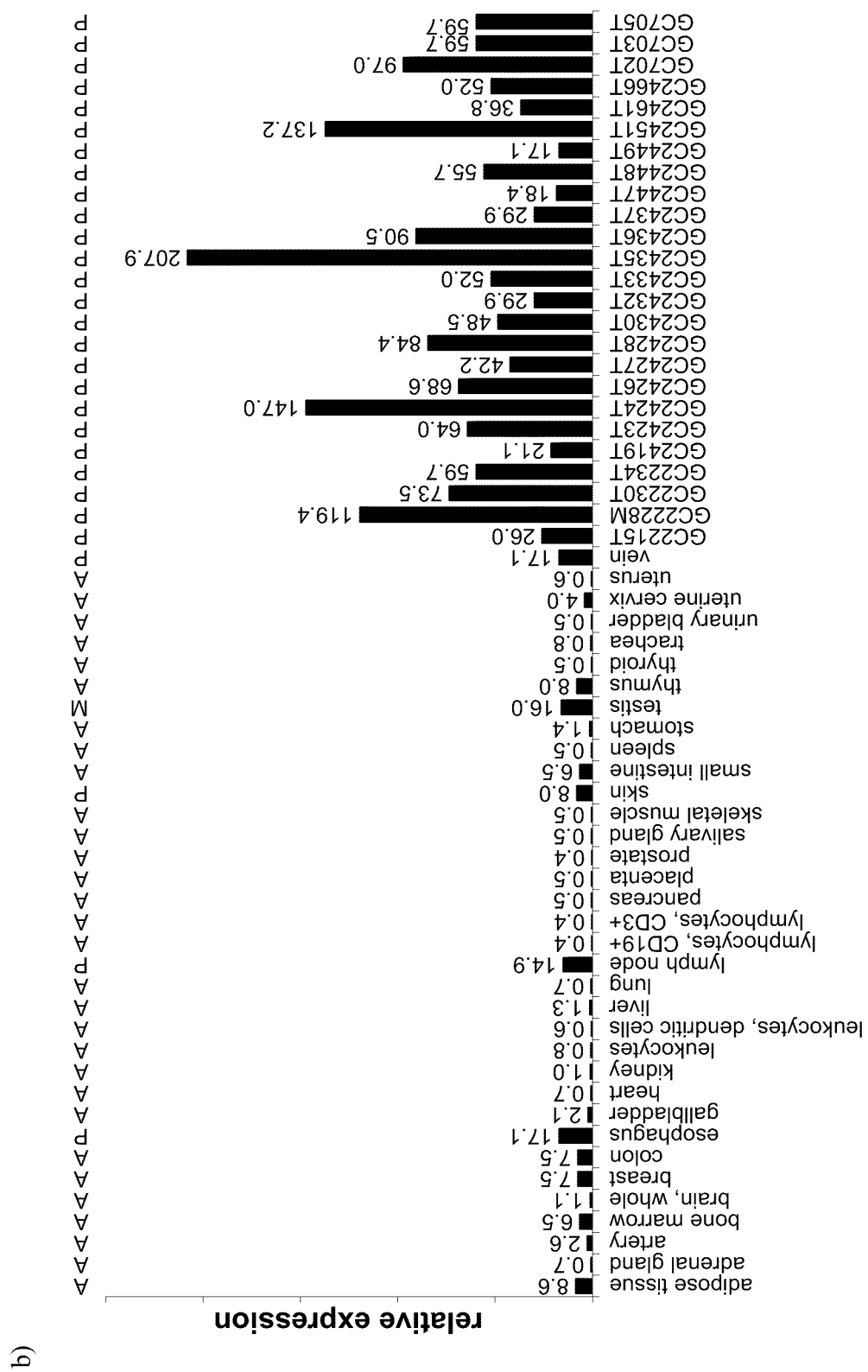

FIG. 2: shows expression profiles of mRNA of selected proteins in normal tissues and in 25 gastric cancer samples; CDC2 (Probeset ID: 203213_at); ASPM (Probeset ID: 219918_s_at).

Figure 3:
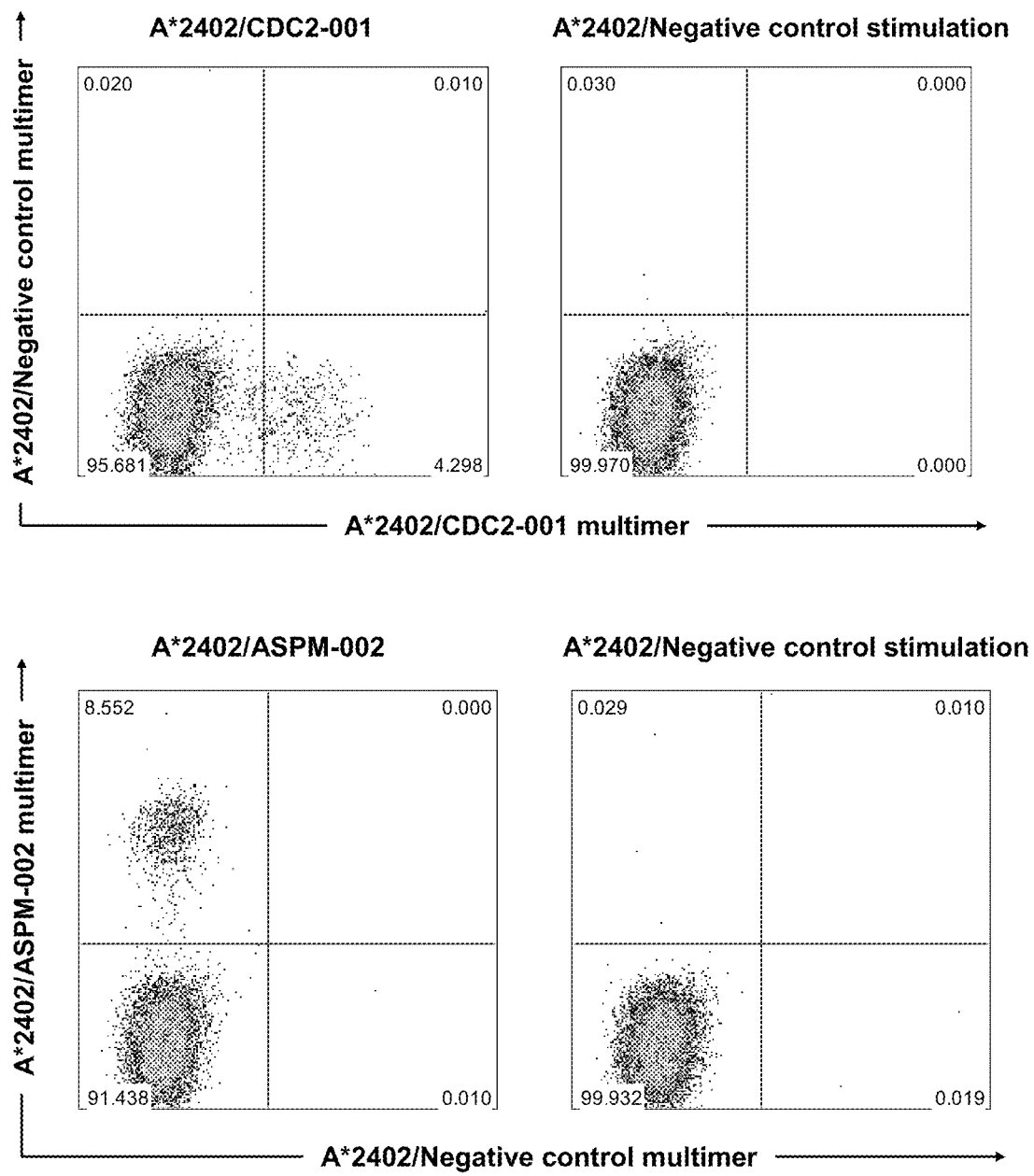
FIG. 3: shows exemplary results of peptide-specific in vitro immunogenicity of class I TUMAPs. CD8+ T cells were primed using artificial APCs loaded with relevant (left panel) and irrelevant peptide (right panel), respectively. After three cycles of stimulation, the detection of peptide-reactive cells was performed by double staining with relevant plus irrelevant A*2402-multimers. Shown cells are gated on live CD8+ lymphocytes and the numbers in the plots represent percentages of multimer-positive cells.

FIG. 3: shows exemplary results of peptide-specific in vitro immunogenicity of class I TUMAPs. CD8+ T cells were primed using artificial APCs loaded with relevant (left panel) and irrelevant peptide (right panel), respectively. After three cycles of stimulation, the detection of peptide-reactive cells was performed by double staining with relevant plus irrelevant A*2402-multimers. Shown cells are gated on live CD8+ lymphocytes and the numbers in the plots represent percentages of multimer-positive cells.

Figure 4:
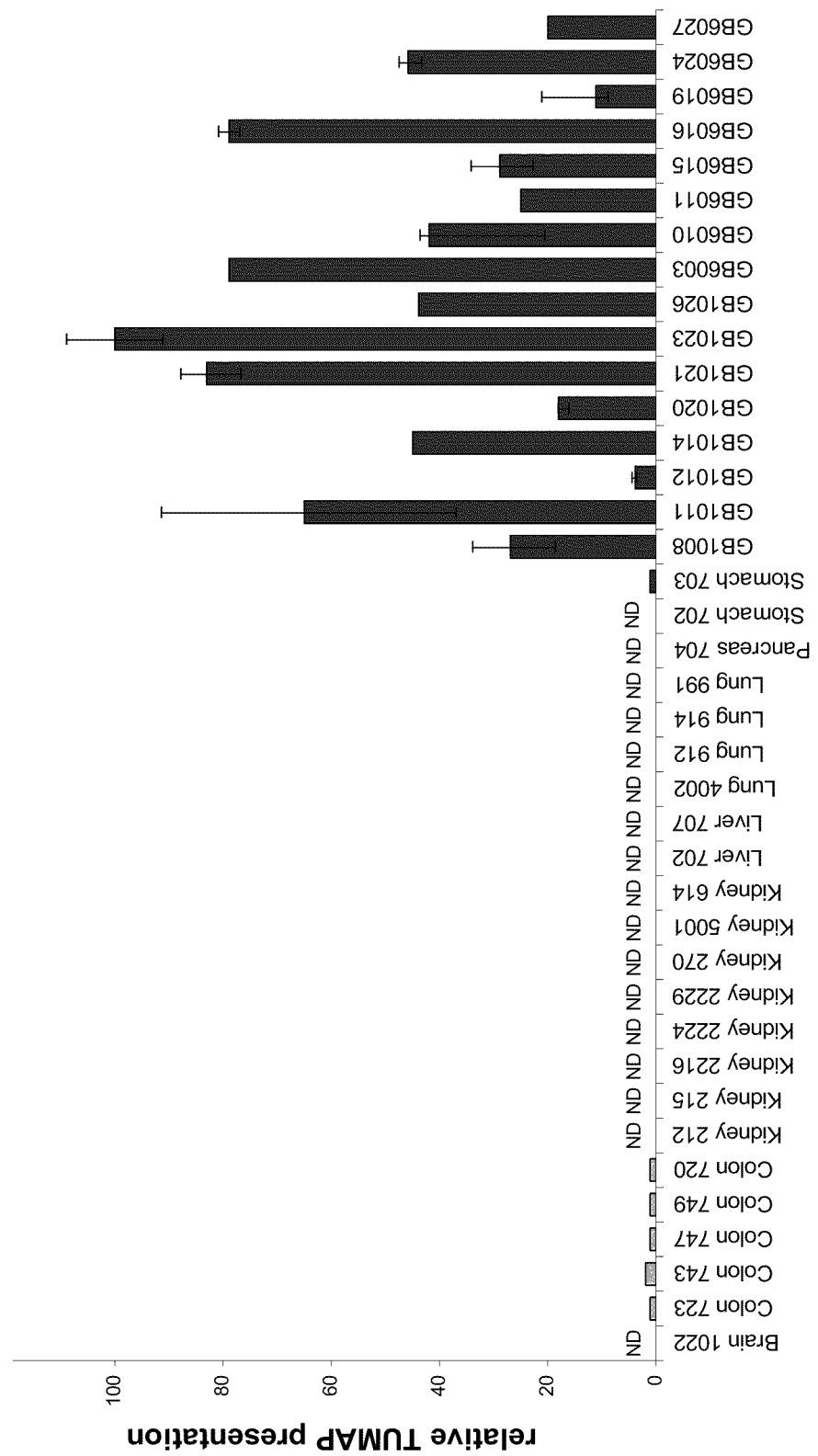
FIG. 4: shows a presentation profile for an HLA class I peptide of PTPRZ1 (tyrosine phosphatase, receptor-type, Z polypeptide 1).

FIG. 4: shows a presentation profile for an HLA class I peptide of PTPRZ1 (tyrosine phosphatase, receptor-type, Z polypeptide 1).

Figure 5:
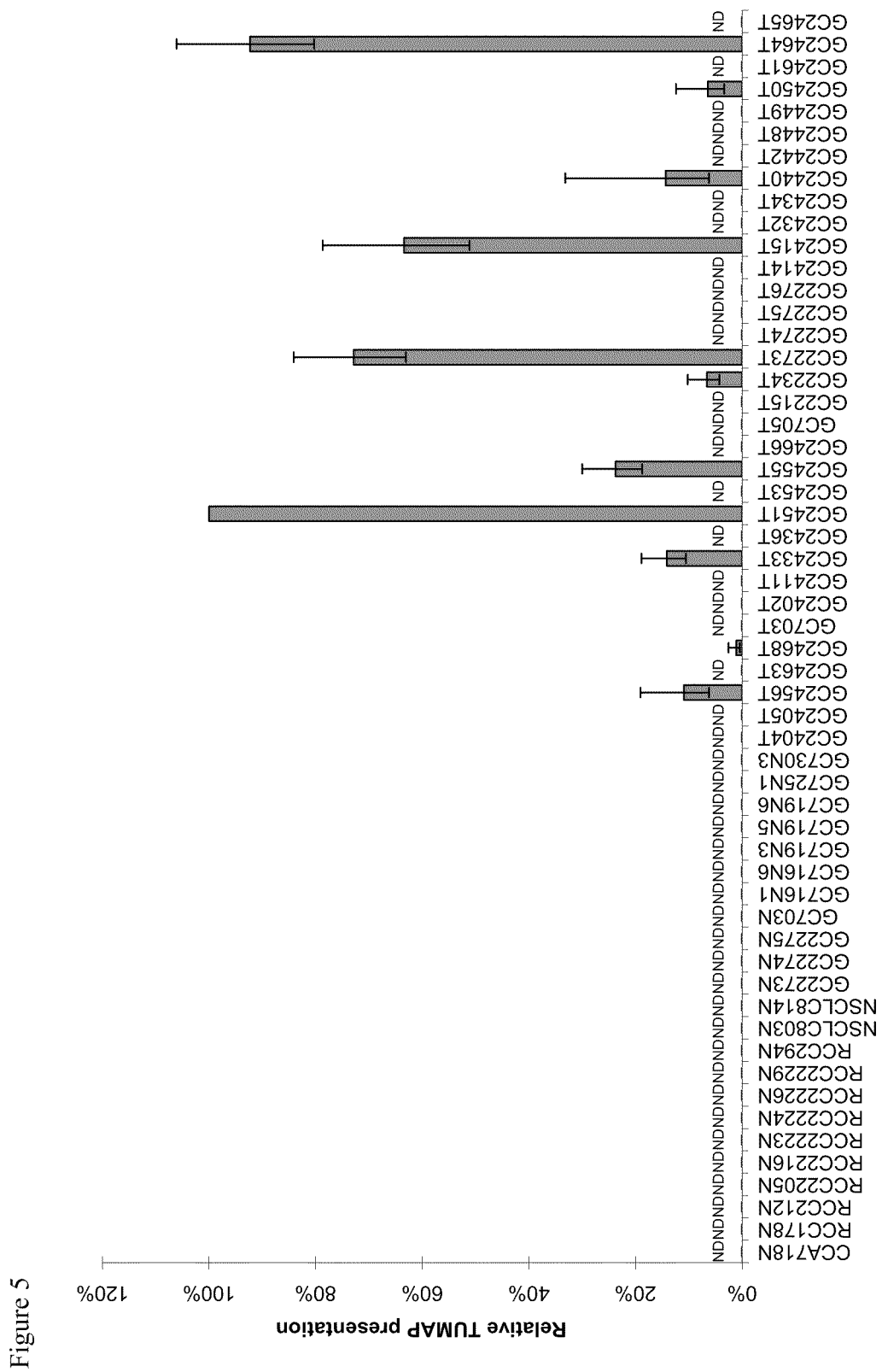
FIG. 5: shows a presentation profile for an HLA class I peptide of CDK1 (cyclin-dependent kinase 1).

FIG. 5: shows a presentation profile for an HLA class I peptide of CDK1 (cyclin-dependent kinase 1).

Figure 6:
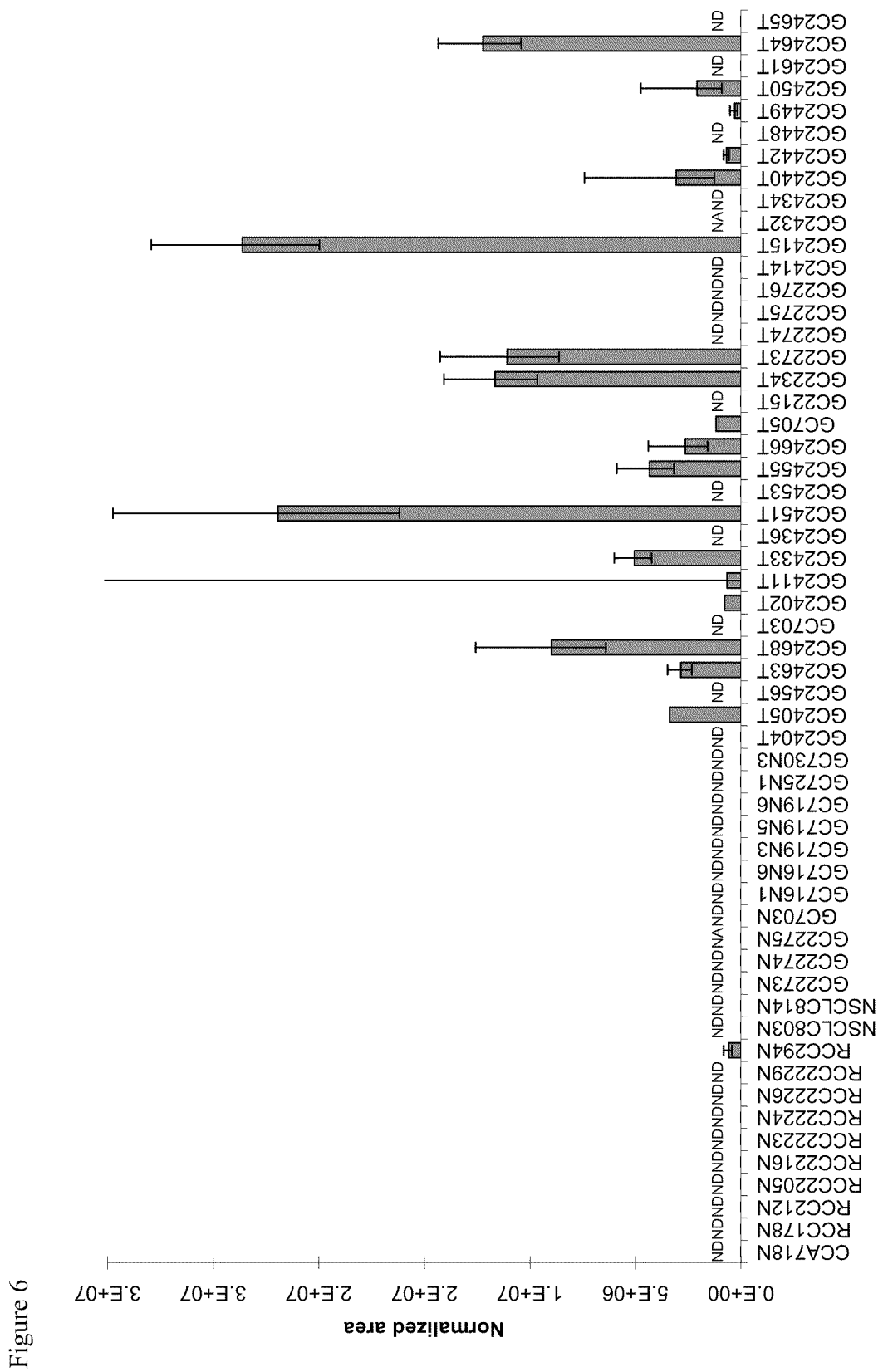
FIG. 6: shows a presentation profile for an HLA class I peptide of ASPM (asp (abnormal spindle) homolog, microcephaly associated (*Drosophila*)).

FIG. 6: shows a presentation profile for an HLA class I peptide of ASPM (asp (abnormal spindle) homolog, microcephaly associated (*Drosophila*)).

Figure 7:
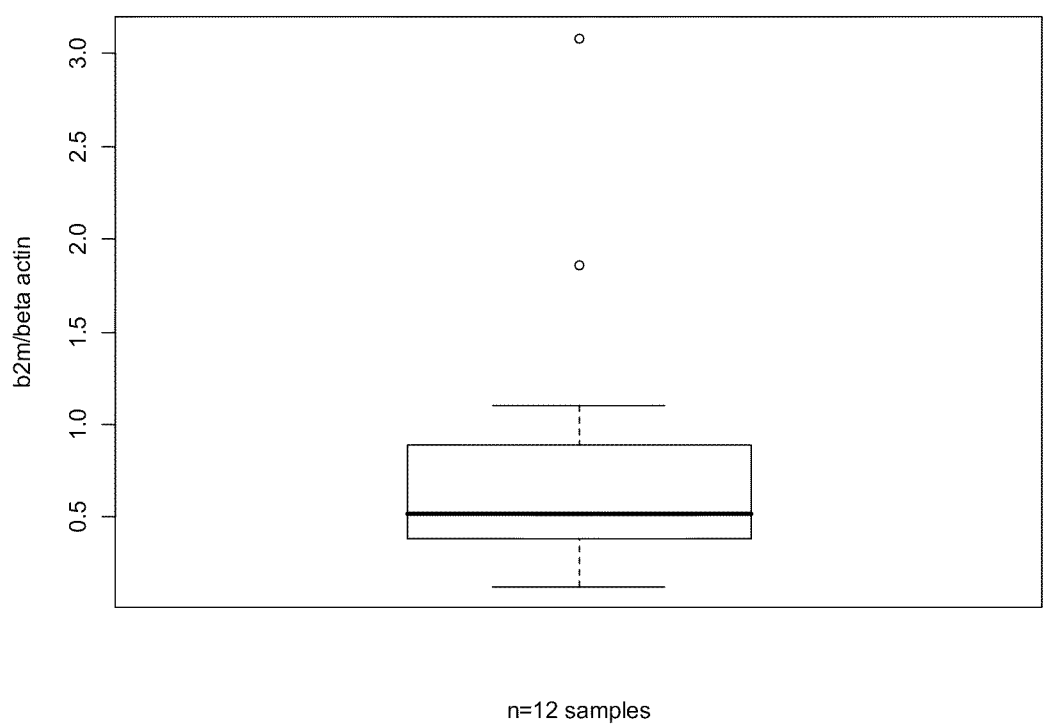
FIG. 7: shows the relative b2m protein expression does not change dominantly in different tissue subtypes.

FIG. 7: shows the relative b2m protein expression does not change dominantly in different tissue subtypes.

Figure 8:
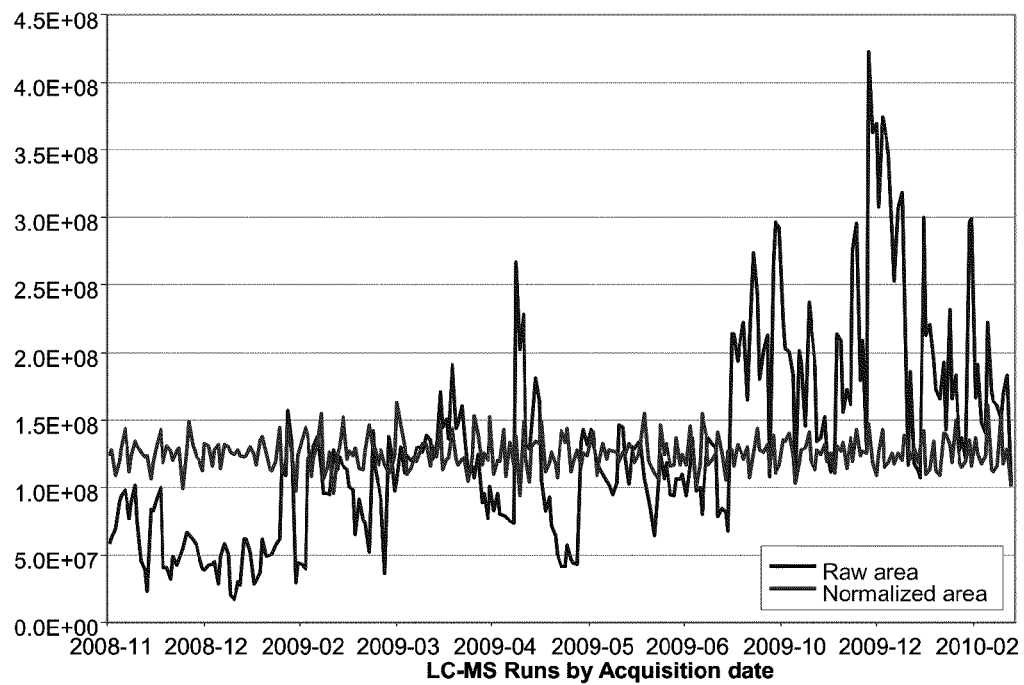
FIG. 8: shows raw and normalized signal areas for spiked synthetic peptide from yeast alcohol dehydrogenase 1. In total, seven spiked peptides covering different retention times, charge states and sequence lengths are used for quality control. The raw areas have been normalized in a two-tier approach accounting for intra- as well as inter-sample variations, e.g. removing bias due to changes in the setup of the mass spectrometer. Differences within the replicates are shown for sample 969 from normal lung tissue.
Figure 8:
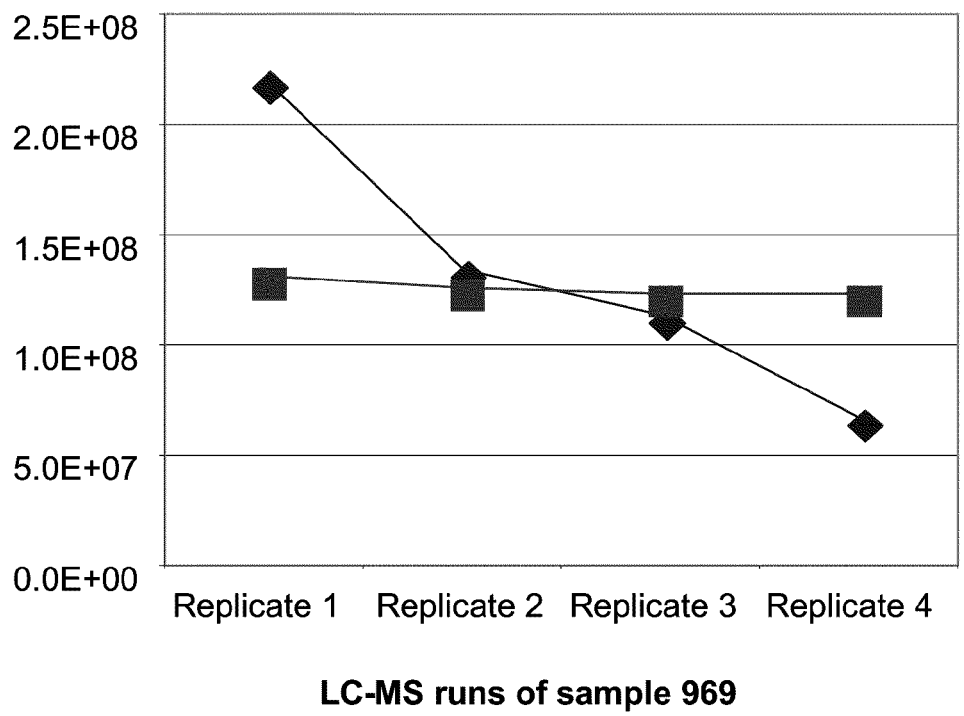

FIG. 8: shows raw and normalized signal areas for spiked synthetic peptide from yeast alcohol dehydrogenase 1. In total, seven spiked peptides covering different retention times, charge states and sequence lengths are used for quality control. The raw areas have been normalized in a two-tier approach accounting for intra- as well as inter-sample variations, e.g. removing bias due to changes in the setup of the mass spectrometer. Differences within the replicates are shown for sample 969 from normal lung tissue.

Figure 9:
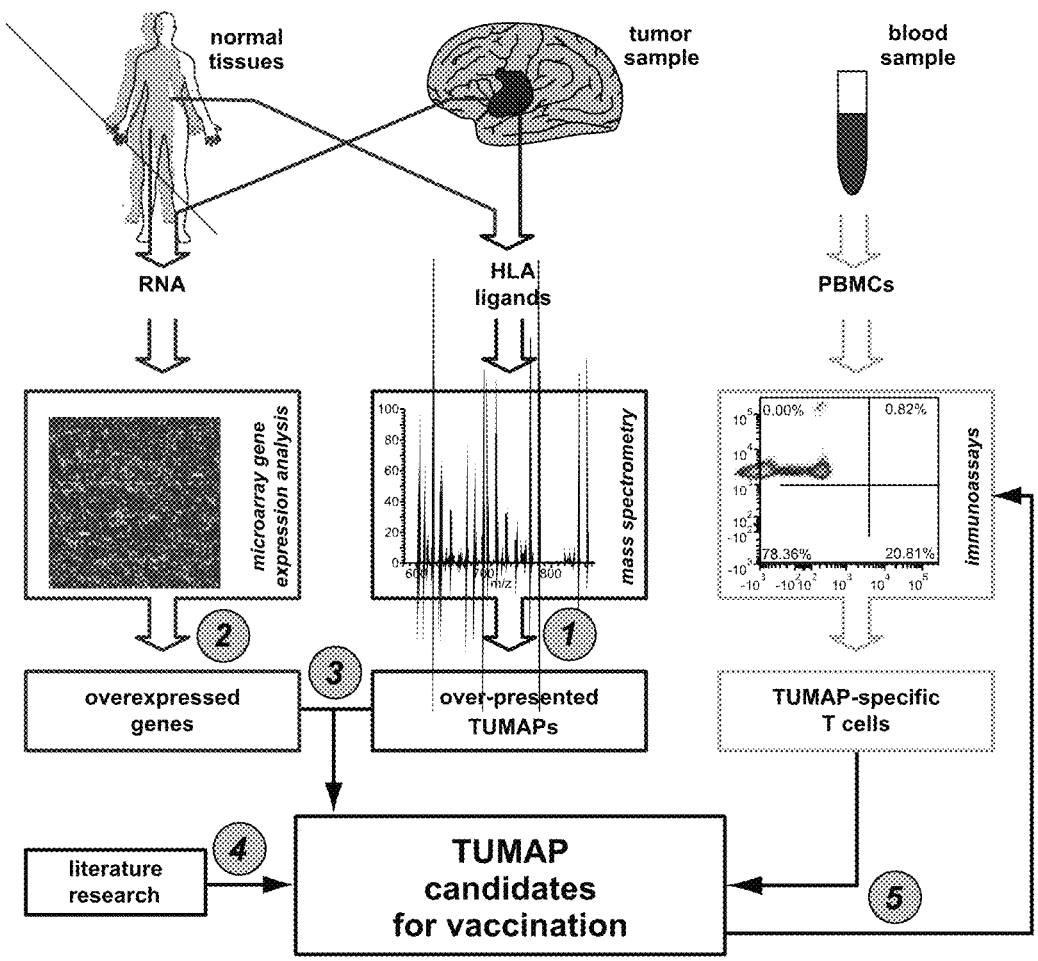
FIG. 9: shows samples from surgically removed normal and tumor tissue as well as blood from healthy donors were analyzed in a stepwise approach.

FIG. 9: shows samples from surgically removed normal and tumor tissue as well as blood from healthy donors were analyzed in a stepwise approach:

1. HLA ligands from the malignant and healthy tissue were identified and differentially quantified by label-free liquid chromatography-coupled mass spectrometry (LCMS) in order to determine over-presented TUMAPs (tumor-associated peptides).

2. Genome-wide messenger ribonucleic acid (mRNA) expression analysis by microarrays was used to identify genes over-expressed in the malignant tissue compared with a range of normal organs and tissues.

3. Identified HLA ligands were compared to gene expression data. Over-presented TUMAPs encoded by selectively expressed or over-expressed genes as detected in step 2 were considered suitable TUMAP candidates for a multi-peptide vaccine.

4. Literature research was performed in order to identify additional evidence supporting the relevance of the identified peptides as TUMAPs and exclude the possibility of the protein playing a crucial role in another pathway.

5. Peripheral T cells from blood of healthy individuals were tested for reactivity against the TUMAP candidates using several immunoassays (in vitro T-cell assays).

FIG. 10: shows a partial LCMS map plotted by OpenMS (M. Sturm and O. Kohlbacher. TOPPView: an open-source viewer for mass spectrometry data. *J Proteome. Res* 8 (7):3760-3763, 2009) with signal for peptide YLLPAIVHI at 122 min.

SEQ ID NO. 1 to 27 show the peptides of table 3 and the examples.

EXAMPLES

The following examples describe the inventive method in the context of TAAs/cancer. The invention is not restricted to the examples, as they are only one preferred embodiment of the invention. For the purposes of the present invention, all references as cited herein are incorporated by reference in their entireties.

Methods:

Tissue Samples

Patients' tumor and normal tissues were provided by several different hospitals depending on the tumor entity analyzed. Written informed consents of all patients had been given before surgery. Tissues were shock-frozen in liquid nitrogen immediately after surgery and stored until isolation of TUMAPs at −80° C.

Isolation of HLA Peptides from Tissue Samples

HLA peptide pools from shock-frozen tissue samples were obtained by immune precipitation from solid tissues according to a slightly modified protocol using the HLA-A, -B, -C-specific antibody W6/32, the HLA-A*02-specific antibody BB7.2, CNBr-activated sepharose, acid treatment, and ultrafiltration. For different HLA-alleles other specific antibodies known in the art can be used as there are for example GAP-A3 for A*03, B1.23.2 for B-alleles.

Mass Spectrometry

The HLA peptide pools as obtained were separated according to their hydrophobicity by reversed-phase chromatography (nanoAcquity UPLC system, Waters) and the eluting peptides were analyzed in an LTQ-Orbitrap hybrid mass spectrometer (ThermoElectron) equipped with an ESI source. Peptide pools were loaded directly onto the analytical fused-silica micro-capillary column (75 μm i.d.×250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometer was operated in the data-dependent mode using a TOP5 and a TOP3 strategy. In brief, a scan cycle was initiated with a full scan of high mass accuracy in the orbitrap (R=30 000 for TOP3, R=60000 for TOP5), which was followed by MS/MS scans either in the Orbitrap (R=7500) on the 5 most abundant precursor ions with dynamic exclusion of previously selected ions (TOP5) or in the LTQ on the 3 most abundant precursor ions with dynamic exclusion of previously selected ions (TOP3).

Data Analysis

For each sample, five label-free replicate LCMS runs have been acquired, two in TOP5 mode and three runs in TOP3 mode. The LCMS data was processed by an in-house pipeline analyzing the LCMS survey as well as the Tandem-MS (MS/MS) data. The proprietary data analysis is optimized and adapted for our incremental, replicate acquisition setting and the peptidomics data which is not handled satisfactory by standard proteomics software. Each new data set is integrated in the Immatics Discovery database (MySQL). All data is cross-referenced to available proteomic, genomic and literature data.

Sequence Identification

Tandem-MS spectra were extracted using msn_extract (ThermoScientific) and searched with Sequest against the IPI database. The protein database hits are subsequently validated by automated quality filtering using thresholds optimized for HLA peptidomics data. Interesting peptide vaccine candidates are further confirmed by manual inspection.

Figure 1:
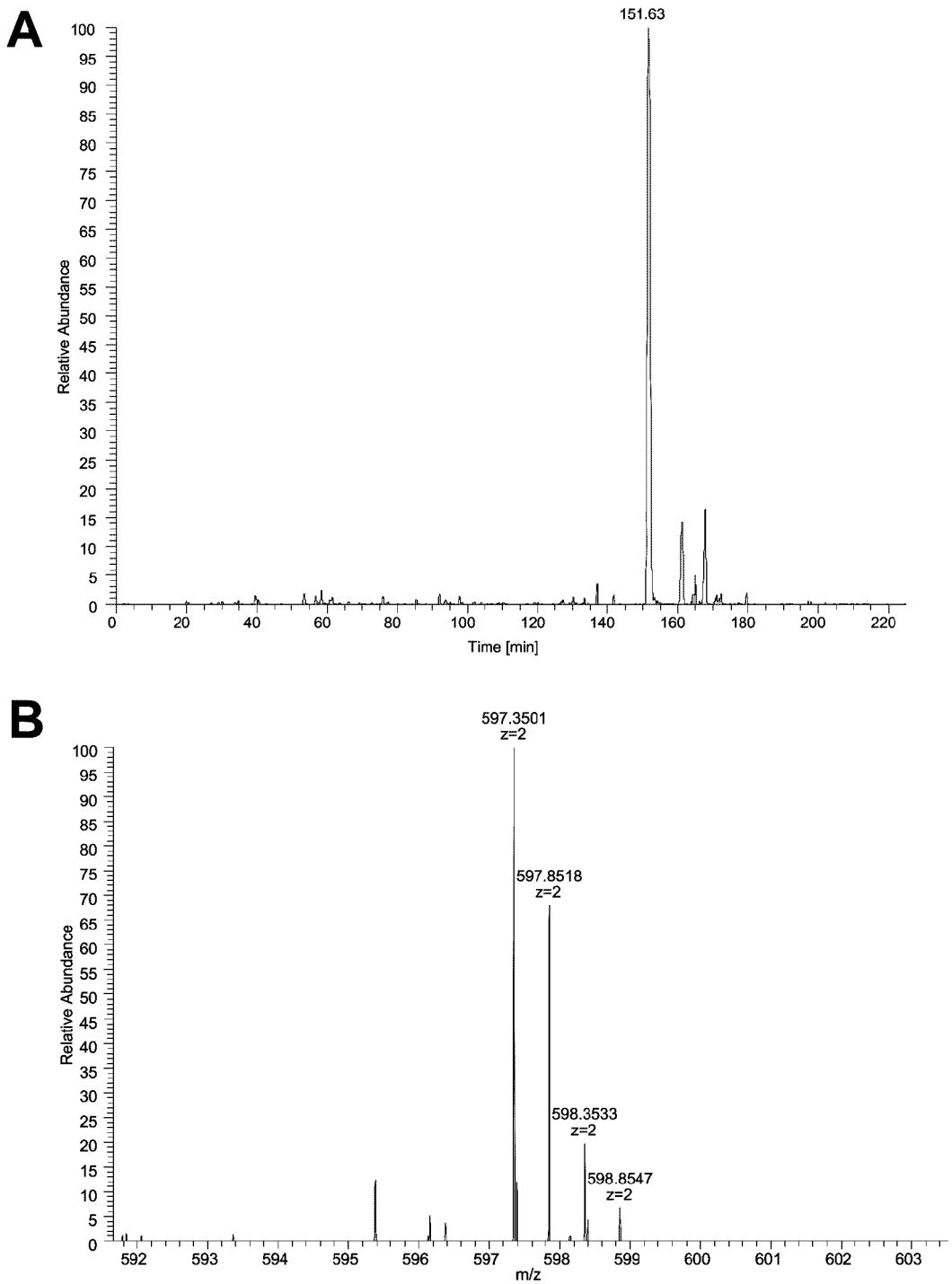
FIG. 1: shows an exemplary mass spectrum from CDC2-001 demonstrating its presentation on primary tumor sample GC2464. NanoESI-LCMS was performed on a peptide pool eluted from the GC sample 2464. The mass chromatogram for m/z 597.3501±0.001 Da, z=2 shows a peptide peak at the retention time 151.63 min. B) The detected peak in the mass chromatogram at 151.63 min revealed a signal of m/z 597.3501 in the MS spectrum. C) A collisionally induced decay mass spectrum from the selected precursor m/z 597.3501 recorded in the nanoESI-LCMS experiment at the given retention time confirmed the presence of CDC2-001 in the GC2464 tumor sample. D) The fragmentation pattern of the synthetic CDC2-001 reference peptide was recorded and compared to the generated natural TUMAP fragmentation pattern shown in C for sequence verification.
Figure 1:
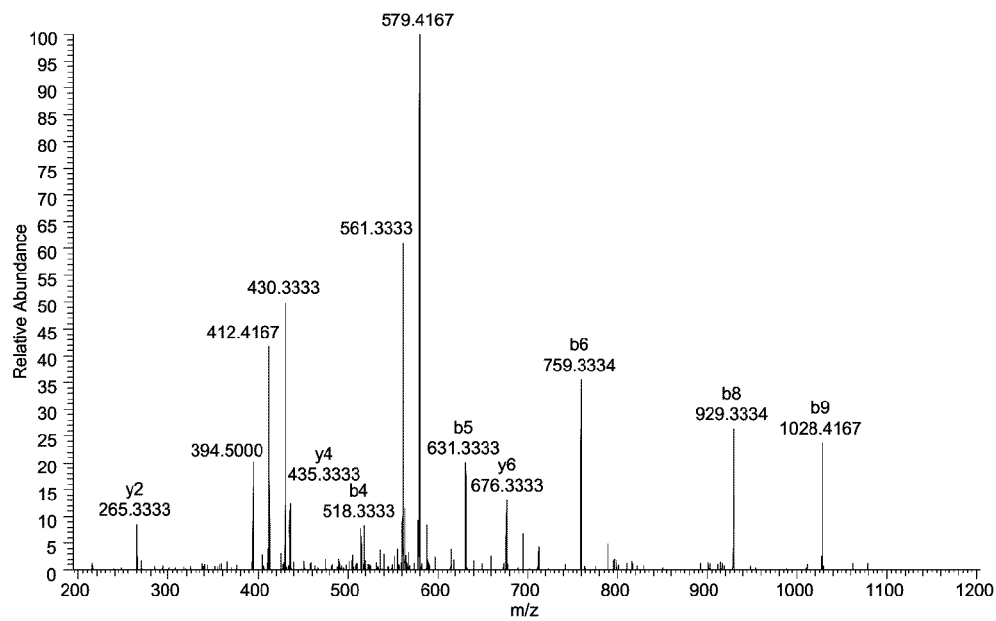
Figure 1:
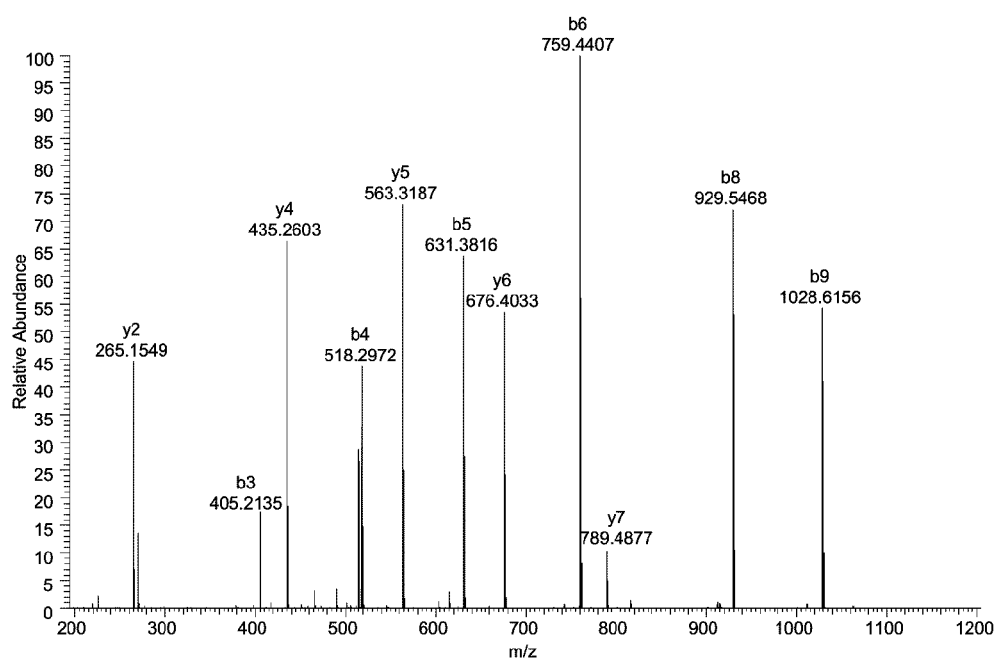

The identified peptide sequence was assured by comparison of the generated natural peptide fragmentation pattern with the fragmentation pattern of a synthetic sequence-identical reference peptide. FIG. 1 shows an exemplary spectrum obtained from tumor tissue for the MHC class I associated peptide CDC2-001 and its elution profile on the UPLC system.

For increased identification sensitivity, an in-house developed spectral clustering algorithm was used to assign spectra to known peptide MS/MS which are being collected in the IFL (Immatics Fragment spectra Library). The MS/MS scans of a new LCMS run are added incrementally to the IFL scan by scan. The clustering uses a growing k-means clustering algorithm adapted for spectral data. Pairwise similarity between scans is measured by MuQest (ThermoScientific). Each cluster is represented by a consensus spectrum. These consensus spectra can be used to speed up downstream analyses by removing the spectral redundancy. Since consensus spectra result from averaging experimental MS/MS spectra, precursor masses are more accurate and the spectra show less noise.

Relative TUMAP Quantification

LCMS survey data was analyzed independently of the Tandem-MS making use of the high-mass accuracy. To extract LCMS signals as well as the signal areas (ion counting) the program SuperHirn (ETH Zurich) was used. Thus each identified peptide can be associated with quantitative data allowing relative quantification between samples and tissues.

To account for variation between technical and biological replicates, a two-tier normalization scheme was used based on central tendency normalization. The normalization assumes that most measured signals result from house-keeping peptides and the small fraction of over-presented peptides does not influence the central tendency of the data significantly. In the first normalization step the replicates of the same sample are normalized by calculating the mean presentation for each peptide in the respective replicate set. This mean is used to compute normalization factors for each peptide and LC-MS run. Averaging over all peptides results in run-wise normalization factors which are applied to all peptides of the particular LCMS run. This approach ensures that systematic intra-sample variation is removed, e.g. due to different injection volumes between the replicate runs.

Only peptides, which have a coefficient of variation smaller than 25% between their replicate areas, are considered in the next normalization step. Again the mean presentation of each peptide is calculated, this time for all samples of a defined preparation antibody (e.g. BB7.2). The mean is used to compute normalization factors for each peptide and sample. Averaging over all peptides results in sample-wise normalization factors, which are applied to all peptides of the particular sample. Systematic bias due to different tissue weights or MHC expression levels is therefore removed.

To extract over-presented peptides, a presentation profile was calculated for each peptide showing the mean sample presentation as well as replicate variations. The profile juxtaposes samples of the tumor entity of interest to a baseline of normal tissue samples. Each of these profiles was consolidated into an over-presentation score by calculating the p-value of a Linear Mixed-Effects Models (GNU R) adjusting for multiple testing by False Discovery Rate. Ranking all peptides by their p-values yields the most promising vaccine candidate from a presentation point of view.

Quantitation of Beta2m-Microglobulin

Beta-2-microglobulin (b2m) was quantified by western blotting, using beta-actin as reference protein to normalize for protein amounts loaded on the gels.

Results

Development of TUMAP Quantitation Using Cell Lines

To establish the quantitation pipeline, different methods have been applied. First a dilution experiment was conducted using the JY cell line in 2 and 20% dilution to simulate sample variation. For each diluted sample three replicates have been acquired. After normalization of inter-run and inter-sample variation the normalization factor between the two samples was 9.95.

In a second experiment another JY sample was spiked with a tryptically digested MassPREP™ (Waters) protein mix (Phosphorylase b, BSA, Bovine Hemoglobin, Enolase, ADH) in 100, 10 and 1 fmol dilutions. Again, three replicates for each concentration were acquired. After data analysis, the mean ratio between the known spiked peptides was 90, 8 and 11 if comparing the 1 versus the 100 fmol sample, 100 vs. 10 fmol and 10 vs. 1 fmol, respectively.

In addition, we compared different acquisition methods to maximize the number and accuracy of peptide identifications as well as the quantitative precision of our setting. For this purpose, we examined about 50 replicates of a JY sample in different MS/MS modes.

Primary Tumor and Normal Tissues

Examples for relatively quantified TUMAPs are shown below.

Example 1

Presentation profile for an HLA class I peptide of PTPRZ1 (tyrosine phosphatase, receptor-type, Z polypeptide 1) which is part of a glioblastoma vaccine cocktail. Shown in red are tumor samples relative to normal tissue samples from different organs. Each bar represents the normalized median sample area for this peptide while the error bars show the minimum and maximum replicate area as indicators for the measurement variation.

Example 2: CDC2-001

For the presentation profile for a gastric cancer associated TUMAP encoded by CDK1, reference is made to FIG. 5.

Example 3: ASPM-002

For the presentation profile for a gastric cancer associated TUMAP encoded by ASPM reference is made to FIG. 6.

MHC Protein Expression in Different Tissue Entities

The inventors analyzed expression of MHC molecules in different tissue entities to know about the range of MHC expression levels using beta-2-microglobulin as representative compound of the ternary MHC alpha chain/beta-2-microglobulin/peptide complex (see FIG. 7).

Relative MHC expression (b2 m/beta actin) varies only by a factor of 5 around the median value b2 m/beta actin=0.52 and thus is relatively constant between different tissue entities. This range is narrow enough for a normalization based on mass spectrometry data.

Normalization of MHC Amounts Based on Mass Spectrometry as Compared to Western Blotting (WB)

TABLE 2

Comparison of WB-based and MS-based normalization of MHC

|  | TC001T | RCC2216N | RCC2216T | RCC2223N | RCC2223T |
|---|---|---|---|---|---|
| Relative WB normaliz. factor | 0.07 | 2.03 | 2.58 | 1.00 | 0.17 |
| Relative MS normaliz. factor | 0.05 | 2.53 | 1.11 | 1.00 | 0.30 |
| Tissue weight [g] | 3.56 | 0.29 | 0.89 | 0.65 | 1.54 |
| IDs for MS normalization | 119 | 540 | 47 | 908 | 877 |

In summary, MS- and WB-based normalization are very comparable; variation between these normalization methods is only by about a factor of 2. The MS normalization factor improves in accuracy if more identifications are used in its calculation. Therefore, MS based normalization is a reliable method for compensating varying amounts of MHC molecules obtained from primary tissue immune precipitations.

Quality Assurance

In order to check the quantitative performance continuously, we established and introduced seven synthetic non-human peptides for quality control of retention time and signal area.

Since each sample is analyzed using five replicates, peptide quantitation is accompanied by estimation of variation to detect measurement problems. Concomitantly, we have established a manual quality control procedure to ensure consistency and correctness of data for peptides entering the validation.

Example for the Determination of the Immunogenicity of the Peptides and the Expression Profiling Expression Profiling of Genes Encoding the Peptides of the Invention Not all peptides identified as being presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. In order to identify such peptides and minimize the risk for autoimmunity induced by vaccination the inventors focused on those peptides that are derived from proteins that are over-expressed on tumor cells compared to the majority of normal tissues.

The ideal peptide will be derived from a protein that is unique to the tumor and not present in any other tissue. To identify peptides that are derived from genes with an expression profile similar to the ideal one the identified peptides were assigned to the proteins and genes, respectively, from which they were derived and expression profiles of these genes were generated.

RNA Sources and Preparation

Surgically removed tissue specimens were provided by two different clinical sites (see Example 1) after written informed consent had been obtained from each patient. Tumor tissue specimens were snap-frozen in liquid nitrogen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted. Leukocytes were isolated from blood samples of four healthy volunteers.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated antistreptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0.

The expression profiles of source genes of the present invention that are highly over-expressed in gastric cancer are shown in FIG. 2.

Example 3

In Vitro Immunogenicity for IMA941 MHC Class I Presented Peptides

To get information regarding the immunogenicity of the TUMAPs of the present invention, we performed investigations using a well established in vitro stimulation platform already described by (Walter, S, Herrgen, L, Schoor, O, Jung, G, Wernet, D, Buhring, H J, Rammensee, H G, and Stevanovic, S; 2003, Cutting edge: predetermined avidity of human CD8 T cells expanded on calibrated MHC/anti-CD28-coated microspheres, J. Immunol., 171, 4974-4978). This way we could show immunogenicity for 32 HLA-A*2402 restricted TUMAPs of the invention demonstrating that these peptides are T-cell epitopes against which CD8+ precursor T cells exist in humans (Table 3).

In Vitro Priming of CD8+ T Cells

In order to perform in vitro stimulations by artificial antigen presenting cells (aAPC) loaded with peptide-MHC complex (pMHC) and anti-CD28 antibody, we first isolated CD8 T cells from fresh HLA-A*24 leukapheresis products of healthy donors obtained from the Blood Bank Tuebingen.

CD8 T cells were either directly enriched from the leukapheresis product or PBMCs (peripheral blood mononuclear cells) were isolated first by using standard gradient separation medium (PAA, Cölbe, Germany). Isolated CD8 lymphocytes or PBMCs were incubated until use in T-cell medium (TCM) consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step. Isolation of CD8+ lymphocytes was performed by positive selection using CD8 MicroBeads (Miltenyi Biotec, Bergisch-Gladbach, Germany).

Generation of pMHC/anti-CD28 coated beads, T-cell stimulations and readout was performed as described before (Walter et al. 4974-78) with minor modifications. Briefly, biotinylated peptide-loaded recombinant HLA-A*2402 molecules lacking the transmembrane domain and biotinylated at the carboxy terminus of the heavy chain were produced. The purified costimulatory mouse IgG2a anti human CD28 Ab 9.3 (Jung, Ledbetter, and Muller-Eberhard 4611-15) was chemically biotinylated using Sulfo-N-hydroxysuccinimidobiotin as recommended by the manufacturer (Perbio, Bonn, Germany). Beads used were 5.6 µm large streptavidin coated polystyrene particles (Bangs Laboratories, Illinois, USA). pMHC used as controls were A*0201/MLA-001 (peptide ELAGIGILTV (SEQ ID No. 26) from modified Melan-A/MART-1) and A*0201/DDX5-001 (YLLPAIVHI (SEQ ID No. 27) from DDX5), respectively.

800.000 beads/200 µl were coated in 96-well plates in the presence of 600 ng biotin anti-CD28 plus 200 ng relevant biotin-pMHC (high density beads). Stimulations were initiated in 96-well plates by co-incubating $1 \times 10^6$ CD8+ T cells with $2 \times 10^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times. Finally, multimeric analyses were performed by staining the cells with Live/dead-Aqua dye (Invitrogen, Karlsruhe, Germany), CD8-FITC antibody clone SK1 (BD, Heidelberg, Germany) and PE- or APC-coupled A*2402 MHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+ CD8+ lymphocytes was detected by appropriate gating and by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for the Peptides

For tested HLA class I peptides, in vitro immunogenicity could be demonstrated for 25 peptides by generation of peptide specific T-cell lines. Exemplary flow cytometry results after TUMAP-specific multimer staining for two peptides of the invention are shown in FIG. 3 together with a corresponding negative control. Results for the 25 peptides from the invention are summarized in Table 3.

TABLE 3

In vitro immunogenicity of HLA class I peptides of the invention

| SEQ ID NO: | Antigen | Sequence | Positive donors/ donors tested [%] | Positive wells/ wells tested [%] |
|---|---|---|---|---|
| 1 | CDC2-001 | LYQILQGIVF | 88 | 28 |
| 2 | ASPM-002 | SYNPLWLRI | 63 | 31 |
| 3 | MMP3-001 | VFIFKGNQF | 13 | 1 |
| 4 | MET-006 | SYIDVLPEF | 63 | 22 |
| 5 | UCHL5-001 | NYLPFIMEL | 75 | 14 |
| 6 | MST1R-001 | NYLLYVSNF | 50 | 14 |
| 7 | KIF2C-001 | IYNGKLFDLL | 13 | 2 |
| 8 | SMC4-001 | HYKPTPLYF | 75 | 9 |
| 9 | PROM1-001 | VWSDVTPLTF | 83 | 26 |
| 10 | MMP11-001 | NYLLYVSNF | 33 | 11 |
| 11 | NFYB-001 | VYTTSYQQI | 50 | 7 |
| 12 | ASPM-001 | RYLWATVTI | 17 | 3 |
| 13 | PLK4-001 | QYASRFVQL | 60 | 5 |
| 14 | ABL1-001 | TYGNLLDYL | 50 | 13 |
| 15 | ATAD2-001 | AYAIIKEEL | 50 | 4 |
| 16 | AVL9-001 | FYISPVNKL | 100 | 50 |
| 17 | HSP90B1-001 | KYNDTFWKEF | 50 | 4 |
| 18 | MUC6-001 | NYEETFPHI | 50 | 21 |
| 19 | NUF2-001 | VYGIRLEHF | 100 | 25 |
| 20 | NUF2-002 | RFLSGIINF | 50 | 4 |
| 21 | PPAP2C-001 | AYLVYTDRL | 100 | 54 |
| 22 | SIAH2-001 | VFDTAIAHLF | 50 | 4 |
| 23 | UQCRB-001 | YYNAAGFNKL | 100 | 38 |
| 24 | IQGAP3-001 | VYKVVGNLL | 100 | 24 |
| 25 | ERBB3-001 | VYIEKNDKL | 83 | 15 |

Results of in vitro immunogenicity experiments conducted by the inventors show the percentage of positive tested donors and wells among evaluable. At least two donors and 24 wells were evaluable for each peptide.

The invention claimed is:

1. A method for the identification and label-free quantification of at least one MHC ligand peptide suitable for use in an immunotherapeutic composition, said method comprising
    a) isolating at least one MHC ligand peptide from at least one primary healthy tissue sample and at least one primary diseased tissue sample by immune-precipitating the at least one MHC ligand peptide using an antibody that specifically binds to a human leukocyte antigen (HLA)-A, HLA-B, and/or HLA-C,
    b) performing an HPLC-MS analysis on said MHC ligand peptides in order to generate peptide signals therefor, wherein a plurality of replicate runs of HPLC-MS analysis is performed for each sample,
    c) extracting the precursor ion signal area for each of said MHC ligand peptide signals,
    d) identifying the sequences for each of said MHC ligand peptides,
    e) normalizing the areas within replicate runs by calculating a mean presentation value for each peptide in each replicate run; and computing a normalization factor for each peptide and each replicate run using the mean presentation value; and averaging over all peptides results in run-wise normalization factors; and applying the run-wise normalization factors to all peptides of a particular replicate run,
    f) determining relative quantities of the MHC ligand peptides that are comparable between samples,
    g) calculating a presentation profile and/or a presentation score for the MHC ligand peptide of said diseased sample and said healthy sample based on said average and relative quantities of the MHC ligand peptide, and
    i) label-free quantification of the MHC ligand peptides,
    j) formulating the at least one MHC ligand peptide in an immunotherapeutic composition if the at least one MHC ligand peptide is over-presented in the diseased sample.

2. The method of claim 1, wherein f) comprises:
    f1) assigning the MHC ligand peptide to an allele-specific sequence subgroup for a comparison between different samples by identifying at least one MHC allele to which the MHC ligand peptide is expected to bind, and
    f2) normalizing between different samples using the allele-specific subgroups to account for different sample sizes and/or MHC expression levels; and
    f3) performing a data quality control based on peptide reproducibility for each sample.

3. The method of claim 1, wherein said method allows handling of tissue samples of different amounts and MHC expression levels.

4. The method of claim 1, wherein said tissue samples comprise primary tissue samples.

5. The method of claim 1, wherein the method is capable of being performed on a high-throughput basis.

6. The method of claim 1, wherein said method is capable of being performed incrementally by increasing an existing dataset from earlier tested samples with data of new samples.

7. The method of claim 1, wherein at least five label-free replicate LCMS runs are performed for each sample.

8. The method of claim 2, wherein normalizing between different samples is performed by a method comprising:
    (f2α) calculating a mean presentation value of each peptide for all samples of a defined preparation antibody;
    (f2β) computing a normalization factor for each peptide and sample using a mean presentation value; and
    (f2γ) averaging over all peptides results in sample-wise normalization factors, and
    (f2δ) applying sample-wise normalization factors to all peptides of the particular sample.

9. The method of claim 1, wherein the presentation score is a p-value of a linear mixed model or a p-value of a t-test.

10. The method of claim 9, wherein the presentation score is adjusted for multiple testing using false discovery rate.

11. The method of claim 1, wherein the sequence is identified by generating a consensus spectrum from the HPLC-MS analysis and at least one previous HPLC-MS analysis.

12. The method of claim 11, further comprising performing fragment spectra clustering, wherein clustering is performed by a growing k-means clustering algorithm.

* * * * *